US008222254B2

(12) United States Patent
Heal et al.

(10) Patent No.: US 8,222,254 B2
(45) Date of Patent: Jul. 17, 2012

(54) 1, 2, 4-TRIAZOLE DERIVATIVES AS SEROTONERGIC MODULATORS

(75) Inventors: Jonathan Richard Heal, Newton (GB); Joseph Michael Sheridan, Newton (GB); William Dennys Ormrod Hamilton, Newton (GB); Simon James Grimshaw, Newton (GB); Sorin Vasile Filip, Newton (GB)

(73) Assignee: Prosarix Limited, Cambridge (GB)

( * ) Notice: Subject to any disclaimer, the term of this patent is extended or adjusted under 35 U.S.C. 154(b) by 88 days.

(21) Appl. No.: 12/670,829

(22) PCT Filed: Aug. 6, 2008

(86) PCT No.: PCT/GB2008/002669
§ 371 (c)(1),
(2), (4) Date: Jun. 21, 2010

(87) PCT Pub. No.: WO2009/019472
PCT Pub. Date: Feb. 12, 2009

(65) Prior Publication Data
US 2010/0261732 A1  Oct. 14, 2010

(30) Foreign Application Priority Data

Aug. 7, 2007 (GB) .................................. 0715378.6
Jun. 4, 2008 (GB) .................................. 0810168.5

(51) Int. Cl.
*A61K 31/496* (2006.01)
*C07D 249/12* (2006.01)
*C07D 401/12* (2006.01)
*C07D 403/12* (2006.01)

(52) U.S. Cl. ......... 514/252.19; 514/253.09; 514/254.05; 514/340; 544/295; 544/364; 544/366; 546/268.4

(58) Field of Classification Search .................. None
See application file for complete search history.

(56) References Cited

U.S. PATENT DOCUMENTS

| 4,487,773 A | 12/1984 | Temple, Jr. et al. |
| 6,124,294 A | 9/2000 | Hellendahl et al. |

FOREIGN PATENT DOCUMENTS
WO     WO 97/03067     1/1997

OTHER PUBLICATIONS

Vippagunta et al Advanced Drug Delivery Reviews, vol. 48, pp. 3-26 (2001).*

Mokrosz, JL et al. "A Search for New Trazodone-Like Antidepressants: Synthesis and Preliminary Receptor Binding Studies" Arch Pharm (Weinhein W Ger), vol. 328, 1995, pp. 623-625.
XP002502432, Abstract, Database Chemcats, Chemical Abstracts Service, Columbus, Ohio, US: AN 2039664876 2008.
XP002502433, Abstract, Database Chemcats, Chemical Abstracts Service, Columbus, Ohio, US: AN 2047531154 2008.
XP002502434, Abstract, Database Chemcats, Chemical Abstracts Service, Columbus, Ohio, US: AN 2047538782 2008.
Bulletin of Haffkine Institute vol. 4, No. 2, 1976, pp. 56-59, Khadse et al.
Journal of Pharmacy and Pharmacology vol. 50, No. 1,1998, pp. 117-124, Papakonstantinou-Garoufalia et al.
STN Registry database, compound RN 331979-33-0, entered database Apr. 20, 2001.
STN Registry database, compound RN 331979-35-2, entered database Apr. 20, 2001.
STN Registry database, compound RN 352445-61-5, entered database Aug. 23, 2001.
STN Registry database, compound RN 416891-51-5, entered database May 16, 2002.
STN Registry database, compound RN 418773-50-9, entered database May 20, 2002.
STN Registry database, compound RN 418775-01-6, entered database May 20, 2002.
STN Registry database, compound RN 418777-53-4, entered database May 20, 2002.
STN Registry database, compound RN 418781-43-8, entered database May 20, 2002.
STN Registry database, compound RN 864425-69-4, entered database Oct. 4, 2005.
STN Registry database, compound RN 864431-41-4, entered database Oct. 4, 2005.

\* cited by examiner

*Primary Examiner* — Emily Bernhardt
(74) *Attorney, Agent, or Firm* — Foley & Lardner LLP

(57) ABSTRACT

The invention relates to novel 5-hydroxytryptamine (5-HT) receptor modulator compounds of formula (I); wherein A, B, $R_1$-$R_5$, T, W, X, Y, Z and m are defined herein, to pharmaceutical compositions comprising these compounds and to their use in the treatment of conditions associated with 5-HT action.

(I)

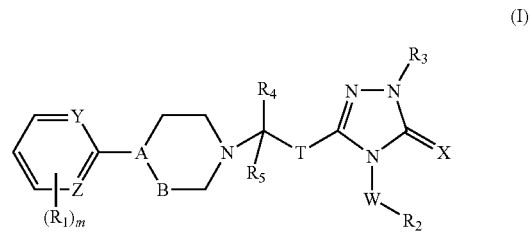

20 Claims, No Drawings

1, 2, 4-TRIAZOLE DERIVATIVES AS SEROTONERGIC MODULATORS

The present application is a 35 U.S.C. 371 national application of PCT/GB2008/002669, filed on Aug. 6, 2008, which claims priority to GB applications 0715378.6 and 0810168.5, filed Aug. 7, 2007, and Jun. 4, 2008, respectively, all of which are hereby incorporated by reference in their entirety.

The invention relates to novel 5-hydroxytryptamine (5-HT) receptor agonist compounds, to pharmaceutical compositions comprising these compounds and to the use of the compounds for the treatment of conditions associated with 5-HT action.

The 5-HT$_{1A}$ receptor is a 5-HT receptor subtype consisting of a 421 amino acid protein with a molecular weight of about 42,000 Daltons. 5-HT$_{1A}$ receptors are located presynaptically in the raphe nuclei, where they act as cell body autoreceptors to inhibit the firing rate of 5-HT neurons, and are located postsynaptically in limbic and cortical regions, where they also attenuate firing activity. Recent studies have indicated that 5-HT$_{1A}$ agonists and partial agonists are particularly relevant to the treatment of anxiety and depression.

Currently, the majority of 5-HT$_{1A}$ agonists are azapirones, e.g. Buspirone (disclosed in U.S. Pat. No. 4,182,763), Gepirone, Zalospirone, Ipsapirone and Tandospirone. However, despite their apparent efficacy, these compounds can cause unpleasant side effects, such as dizziness, fatigue, nausea, nervousness, light-headedness and restlessness. Furthermore, the azapirones also suffer from rapid metabolism leading to a very short elimination half-life (~2-3 h), which necessitates a twice daily dosing regime.

In addition, U.S. Pat. No. 4,487,773 discloses phenoxylalkyl substituted-1,2,4-triazolones having anti-depressant properties (including 3H-1,2,4-triazole-3-one, 5-[3-[4-(3-chlorophenyl)-1-piperazinyl]propyl]-4-ethyl-2,4-dihydro which is described as an intermediate), and WO 2004/069794 discloses arylpiperazinyl sulphonamide compounds, and uses thereof for treating diseases including those mediated directly or indirectly by 5-HT receptors. Khadse, B. G. et al (1976) Bull Haff Instt 4(2), 1-4 discloses 3-mercapto-4-(p-chlorophenyl)-5[N-(p-chlorophenyl)-N-piperazinomethyl]-1,2,4-triazole as an example of an antibacterial agent.

Papakonstantinou-Garoufalia, S. S. et al (1998) J. Pharm. Pharmacol. 50, 117-124 discloses 4-(2,4-dichlorophenyl)-5-[[4-(4-nitrophenyl-1-piperazinyl]methyl]-4H-1,2,4-triazole-3-thiol, 4-(2,4-dichlorophenyl)-5-[[4-(4-methoxyphenyl-1-piperazinyl]methyl]-4H-1,2,4-triazole-3-thiol and 4-(2,4-dichlorophenyl)-5-[[4-(2-methoxyphenyl)-1-piperazinyl]methyl]-4H-1,2,4-triazole-3-thiol as potential antiviral agents.

Certain triazolone intermediates are also listed in chemical abstract databases with no associated with reference or uses, for example: 3H-1,2,4-triazole-3-thione, 2,4-dihydro-5-[2-[4-(2-methoxyphenyl)-1-piperazinyl]ethyl]-4-phenyl (CAS Registry No. RN 418780-84-4), 3H-1,2,4-triazole-3-thione, 5-[2-[4-chlorophenyl)-1-piperazinyl]ethyl]-2,4-dihydro-4-phenyl (CAS Registry No. 418785-15-6) and 3H-1,2,4-triazole-3-thione, 5-[[4-[3-chloro-5-(trifluoromethyl)-2-pyridinyl]-1-piperazinyl]methyl-2,4-dihydro-4-phenyl (CAS Registry No. 338979-15-0).

It is therefore an object of the invention to provide further 5-HT$_{1A}$ agonist compounds.

According to a first aspect of the invention there is provided a compound of formula (I) or a pharmaceutically acceptable salt, solvate or hydrate thereof:

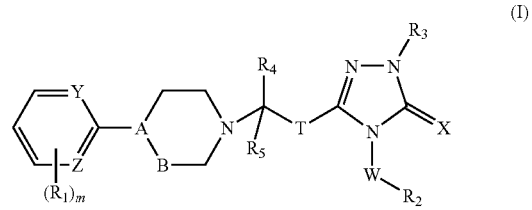

wherein
each $R^1$ independently represents halogen, —CF$_3$, —NO$_2$, C$_{1-6}$ alkoxy, —NR$^6$COR$^7$ or —NR$^6$SO$_2$R$^7$;
m represents an integer from 1 to 2, such that when m represents 2, said $R^1$ groups are not both —NR$^6$COR$^7$ or both —NR$^6$SO$_2$R$^7$ or both —NO$_2$;
$R^2$ represents C$_{1-6}$ alkyl, aryl, or C$_{3-8}$ cycloalkyl, wherein said aryl may be optionally substituted by one or more (e.g. 1 or 2) $R^8$ substituents;
$R^3$, $R^4$, $R^5$, $R^6$ and $R^7$ independently represent hydrogen or C$_{1-6}$ alkyl;
$R^8$ represents halogen, —COOH, C$_{1-6}$ alkyl, or C$_{1-6}$ alkoxy;
-A-B— represents —C═CH— or —N—CH$_2$—;
T represents a linker selected from —(CH$_2$)$_n$— and C$_{3-8}$ cycloalkyl;
n represents an integer from 0 to 4;
X represents an O or S atom;
Y and Z independently represent a CH or N atom;
W represents a bond, or a linker selected from —C(R$^9$)(R$^{10}$)— and C$_{3-8}$ cycloalkyl, wherein R$^9$ and R$^{10}$ independently represent hydrogen, C$_{1-6}$ alkyl or aryl; with the proviso that the compound of formula (I) is not:
3H-1,2,4-triazole-3-thione, 2,4-dihydro-5-[2-[4-(2-methoxyphenyl)-1-piperazinyl]ethyl]-4-phenyl;
3H-1,2,4-triazole-3-thione, 5-[2-[4-chlorophenyl)-1-piperazinyl]ethyl]-2,4-dihydro-4-phenyl;
3H-1,2,4-triazole-3-thione, 5-[[4-[3-chloro-5-(trifluoromethyl)-2-pyridinyl]-1-piperazinyl]methyl-2,4-dihydro-4-phenyl;
3H-1,2,4-triazole-3-one, 5-[3-[4-(3-chlorophenyl)-1-piperazinyl]propyl]-4-ethyl-2,4-dihydro;
4-(2,4-dichlorophenyl)-5-[[4-(4-nitrophenyl-1-piperazinyl]methyl]-4H-1,2,4-triazole-3-thiol;
4-(2,4-dichlorophenyl)-5-[[4-(4-methoxyphenyl-1-piperazinyl]methyl]-4H-1,2,4-triazole-3-thiol;
4-(2,4-dichlorophenyl)-5-[[4-(2-methoxyphenyl)-1-piperazinyl]methyl]-4H-1,2,4-triazole-3-thiol; or
3-mercapto-4-(p-chlorophenyl)-5[N-(p-chlorophenyl)-N-piperazinomethyl]-1,2,4-triazole.

Advantageously, the compounds of formula (I) have been found to be 5-HT agonists, for example 5-HT, receptors agonists, such as 5-HT$_{1A}$, 5-HT$_{1B}$, 5-HT$_{1C}$, 5-HT$_{1D}$, 5-TH$_{1E}$ or 5-HT$_{1F}$ agonists, for instance 5-HT$_{1A}$ agonists, that can be used for the treatment of disorders or conditions associated with 5-HT action. In addition to exhibiting 5-HT$_{1A}$ receptor agonist activity, certain compounds of formula (I) also exhibit dopamine D2 receptor antagonist activity.

In particular, it has been discovered that certain compounds are very active at the 5-HT$_{1A}$ receptor, and are not metabolised rapidly. Thus, certain compounds demonstrate an increased stability half life in cell based experiments, which may allow for reduced dosing requirements for disorders or conditions associated with 5-HT action.

Furthermore, certain compounds of formula (I) are highly selective for 5-HT receptors, with little or no affinity for other receptors, such as α-adrenergic and dopamine D2 receptors, thus reducing the risk of biological side effects. In one embodiment, certain compounds of formula (I) have greater than 10 fold selectivity for the 5-HT$_{1A}$ receptor with respect to the α-adrenergic and dopamine D2 receptor. In a further embodiment, certain compounds of formula (I) have greater than 50 fold selectivity for the 5-HT$_{1A}$ receptor with respect to the α-adrenergic and dopamine D2 receptor. In a yet further embodiment, certain compounds of formula (I) have greater than 100 fold selectivity for the 5-HT$_{1A}$ receptor with respect to the α-adrenergic and dopamine D2 receptor. In a still yet further embodiment, certain compounds of formula (I) have greater than 1000 fold selectivity for the 5-HT$_{1A}$ receptor with respect to the dopamine D2 receptor.

The term 'C$_{1-6}$ alkyl' as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term 'C$_{1-6}$ alkoxy' as used herein refers to an —O—C$_{1-6}$ alkyl group wherein C$_{1-6}$ alkyl is as defined herein. Examples of such groups include methoxy, ethoxy, propoxy, butoxy, pentoxy or hexoxy and the like.

The term 'C$_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term 'halogen' as used herein refers to a fluorine, chlorine, bromine or iodine atom.

The term 'aryl' as used herein refers to a C$_{6-12}$ monocyclic or bicyclic hydrocarbon ring wherein at least one ring is aromatic. Examples of such groups include phenyl, indyl or naphthyl and the like.

According to one particular aspect of the invention there is provided a compound of formula (I):

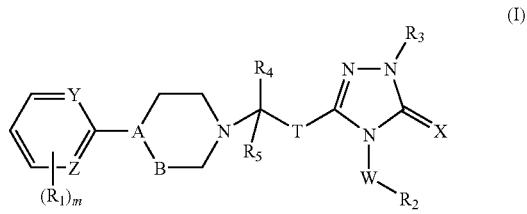

wherein
each R$^1$ independently represents halogen, —CF$_3$, —NO$_2$, C$_{1-6}$ alkoxy, —NR$^6$COR$^7$ or —NR$^6$SO$_2$R$^7$;
m represents an integer from 1 to 2, such that when m represents 2, said R$^1$ groups are not both —NR$^6$COR$^7$ or both —NR$^6$SO$_2$R$^7$ or both —NO$_2$;
R$^2$ represents C$_{1-6}$ alkyl, aryl, or C$_{3-8}$ cycloalkyl, wherein said aryl may be optionally substituted by one or more (e.g. 1 or 2) R$^8$ substituents;
R$^3$, R$^4$, R$^5$, R$^6$ and R$^7$ independently represent hydrogen or C$_{1-6}$ alkyl;
R$^8$ represents halogen, —COOH, C$_{1-6}$ alkyl, or C$_{1-6}$ alkoxy;
-A-B— represents —C═CH— or —N—CH$_2$—;
T represents a linker selected from —(CH$_2$)$_n$— and C$_{3-8}$ cycloalkyl;
n represents an integer from 0 to 4;
X represents an O or S atom;
Y and Z independently represent a CH or N atom;
W represents a bond, or a linker selected from —C(R$^9$)(R$^{10}$)— and C$_{3-8}$ cycloalkyl, wherein R$^9$ and R$^{10}$ independently represent hydrogen, C$_{1-6}$ alkyl or aryl;
or a pharmaceutically acceptable salt, solvate or hydrate thereof.

In one embodiment, R$^1$ is present at the ortho and/or meta position.

In one embodiment, R$^1$ represents C$_{1-6}$ alkoxy, —NR$^6$COR$^7$, or —NR$^6$SO$_2$R$^7$. In a further embodiment, R$^1$ represents methoxy, ethoxy, —CH$_3$CONH$_2$ (ethanamide) or —CH$_3$SO$_2$NH$_2$ (methanesulfonamide). In a further embodiment, R$^1$ represents —NR$^6$COR$^7$ (e.g. 3-NHCOCH$_3$). In a further embodiment, R$^1$ represents-methoxy (e.g. 2-methoxy). In a yet a further embodiment, R$^1$ represents-ethanamide (e.g. 3-ethanamide).

In one embodiment, R$^2$ represents C$_{1-6}$ alkyl (e.g. methyl) or C$_{3-8}$ cycloalkyl (e.g. cyclopentyl, cyclohexyl, cycloheptyl or cyclooctyl). In another embodiment, R$^2$ represents aryl (e.g. naphthyl or indyl or phenyl). In yet another embodiment, R$^2$ represents a phenyl group optionally substituted by one or more (e.g. 1 or 2) R$^8$ substituents.

In one embodiment, R$^8$ represents fluorine, chlorine, bromine, —COOH, methyl, propyl (e.g. isopropyl), butyl (e.g. tert-butyl), methoxy, or ethoxy.

In one embodiment, R$^3$ represents C$_{1-6}$ alkyl (e.g. methyl, ethyl, or isopropyl). In a further embodiment, R$^3$ represents methyl or ethyl. In a yet further embodiment, R$^3$ represents methyl.

In one embodiment, R$^4$ represents hydrogen or methyl. In a further embodiment, R$^4$ represents hydrogen.

In one embodiment, R$^5$ represents hydrogen.

In one embodiment, -A-B— represents —N—CH$_2$—.

In one embodiment, T represents —(CH$_2$)$_n$— (e.g. —(CH$_2$)—, —(CH$_2$)$_2$— or —(CH$_2$)$_3$—). In a further embodiment, T represents —(CH$_2$)—. In a yet further embodiment, T represents a group other than —(CH$_2$)$_2$—. In a yet further embodiment, T represents —(CH$_2$)$_3$—.

In one embodiment, X represents an O atom.

In one embodiment, Y and Z both represent —CH—.

In one embodiment, W represents a bond, or a linker selected from —CH$_2$—, —CH(CH$_3$)—, —CH(CH$_2$CH$_5$)—, —CH(C$_6$H$_5$)— and cyclopropyl. In one embodiment, W represents —CH$_2$— and R$^2$ represents C$_{3-8}$ cycloalkyl (e.g. cyclohexyl).

In one embodiment, m represents 1.

In one embodiment, there is provided a compound selected from, but not limited to, the following compounds:
4-Ethyl-5-{2-[4-(2-methoxyphenyl)piperazino]ethyl}-2,4-dihydro-3H-1,2,4-triazol-3-one (E1);
4-Phenyl-5-{2-[4-(2-methoxyphenyl)piperazino]ethyl}-2,4-dihydro-3H-1,2,4-triazol-3-one (E2);
4-Phenyl-2-ethyl-5-{2-[4-(2-methoxyphenyl)piperazino]ethyl}-2,4-dihydro-3H-1,2,4-triazol-3-one (E3);
4-Phenyl-2-(isopropyl)-5-{2-[4-(2-methoxyphenyl)piperazino]ethyl}-2,4-dihydro-3H-1,2,4-triazol-3-one (E4);
4-(4-Methoxyphenyl)-5-{2-[4-(2-methoxyphenyl)piperazino]ethyl}-2,4-dihydro-3H-1,2,4-triazol-3-one (E5);
4-(4-Chlorophenyl)-5-{2-[4-(2-methoxyphenyl)piperazino]ethyl}-2,4-dihydro-3H-1,2,4-triazol-3-one (E6);
4-Cyclopentyl-5-{2-[4-(2-methoxyphenyl)piperazino]ethyl}-2,4-dihydro-3H-1,2,4-triazol-3-one (E7);
4-Cyclohexyl-5-{2-[4-(2-methoxyphenyl)piperazino]ethyl}-2,4-dihydro-3H-1,2,4-triazol-3-one (E8);
4-(Cyclooctyl)-5-{2-[4-(2-methoxyphenyl)piperazino]ethyl}-2,4-dihydro-3H-1,2,4-triazol-3-one (E9);
4-Cyclooctyl-5-{2-[4-(2-methoxyphenyl)piperazino]ethyl}-2,4-dihydro-3H-1,2,4-triazol-3-one (E10);

4-(2-Napthyl)-5-{2-[4-(2-methoxyphenyl)piperazino]ethyl}-2,4-dihydro-3H-1,2,4-triazol-3-one (E11);
4-(4-Methylphenyl)-5-{2-[4-(2-methoxyphenyl)piperazino]ethyl}-2,4-dihydro-3H-1,2,4-triazol-3-one (E12);
4-(Benzyl)-5-{2-[4-(2-methoxyphenyl)piperazino]ethyl}-2,4-dihydro-3H-1,2,4-triazol-3-one (E13);
4-(4-Isopropylphenyl)-5-{2-[4-(2-methoxyphenyl)piperazino]ethyl}-2,4-dihydro-3H-1,2,4-triazol-3-one (E14);
4-(4-Tertbutylphenyl)-5-{2-[4-(2-methoxyphenyl)piperazino]ethyl}-2,4-dihydro-3H-1,2,4-triazol-3-one (E15);
4-(2,3-Dihydro-1H-inden-4-yl)-5-{2-[4-(2-methoxyphenyl)piperazino]ethyl}-2,4-dihydro-3H-1,2,4-triazol-3-one (E16);
4-(Cyclohexylmethyl)-5-{2-[4-(2-methoxyphenyl)piperazino]ethyl}-2,4-dihydro-3H-1,2,4-triazol-3-one (E17);
4-(1-Phenylethyl)-5-{2-[4-(2-methoxyphenyl)piperazino]ethyl}-2,4-dihydro-3H-1,2,4-triazol-3-one (E18);
4-(1-Phenylpropyl)-5-{2-[4-(2-methoxyphenyl)piperazino]ethyl}-2,4-dihydro-3H-1,2,4-triazol-3-one (E19);
4-(4-Chlorobenzyl)-5-{2-[4-(2-methoxyphenyl)piperazino]ethyl}-2,4-dihydro-3H-1,2,4-triazol-3-one (E20);
4-(3,4-Dichlorobenzyl)-5-{2-[4-(2-methoxyphenyl)piperazino]ethyl}-2,4-dihydro-3H-1,2,4-triazol-3-one (E21);
4-(2-Ethoxybenzyl)-5-{2-[4-(2-methoxyphenyl)piperazino]ethyl}-2,4-dihydro-3H-1,2,4-triazol-3-one (E22);
4-(2-Phenylcyclopropyl)-5-{2-[4-(2-methoxyphenyl)piperazino]ethyl}-2,4-dihydro-3H-1,2,4-triazol-3-one (E23);
4-(2-Methylbenzyl)-5-{2-[4-(2-methoxyphenyl)piperazino]ethyl}-2,4-dihydro-3H-1,2,4-triazol-3-one (E24);
4-(2,4-Dichlorobenzyl)-5-{2-[4-(2-methoxyphenyl)piperazino]ethyl}-2,4-dihydro-3H-1,2,4-triazol-3-one (E25);
4-(3-Fluorobenzyl)-5-{2-[4-(2-methoxyphenyl)piperazino]ethyl}-2,4-dihydro-3H-1,2,4-triazol-3-one (E26);
4-(4-Methylbenzyl)-5-{2-[4-(2-methoxyphenyl)piperazino]ethyl}-2,4-dihydro-3H-1,2,4-triazol-3-one (E27);
4-(Diphenylmethyl)-5-{2-[4-(2-methoxyphenyl)piperazino]ethyl}-2,4-dihydro-3H-1,2,4-triazol-3-one (E28);
4-(2,3-Dihydro-1H-inden-1-yl)-5-{2-[4-(2-methoxyphenyl)piperazino]ethyl}-2,4-dihydro-3H-1,2,4-triazol-3-one (E29);
4-(2-Fluorobenzyl)-5-{2-[4-(2-methoxyphenyl)piperazino]ethyl}-2,4-dihydro-3H-1,2,4-triazol-3-one (E30);
4-(3-Methoxybenzyl)-5-{2-[4-(2-methoxyphenyl)piperazino]ethyl}-2,4-dihydro-3H-1,2,4-triazol-3-one (E31);
4-(2-Chlorobenzyl)-5-{2-[4-(2-methoxyphenyl)piperazino]ethyl}-2,4-dihydro-3H-1,2,4-triazol-3-one (E32);
4-(3,4-Dichlorophenyl)-5-{2-[4-(2-methoxyphenyl)piperazino]ethyl}-2,4-dihydro-3H-1,2,4-triazol-3-one (E33);
4-(4-Bromophenyl)-5-{2-[4-(2-methoxyphenyl)piperazino]propyl}-2,4-dihydro-3H-1,2,4-triazol-3-one (E34);
4-[5-Oxo-3-[(2-methoxyphenyl)piperazin-1-yl)ethyl]-1,5-dihydro-4H-1,2,4-triazol-4-yl]benzoic acid (E35);
4-(Cyclohexylmethyl)-5-{2-[4-(2-methoxyphenyl)piperazino]propyl}-2,4-dihydro-3H-1,2,4-triazol-3-one (E36);
4-(Cyclohexylmethyl)-5-{2-[4-(2-methoxyphenyl)piperazino]propyl}-2-methyl-2,4-dihydro-3H-1,2,4-triazol-3-one (E37);
N-[3-(4-{2-[4-(Cyclohexylmethyl)-5-oxo-4,5-dihydro-1H-1,2,4-triazol-3-yl]ethyl}piperazin-1-yl)phenyl]acetamide (E38);
N-[3-(4-{3-[4-(Cyclohexylmethyl)-5-oxo-4,5-dihydro-1H-1,2,4-triazol-3-yl]propyl}piperazin-1-yl)phenyl]acetamide (E39);
N-[3-(4-{4-[4-(Cyclohexylmethyl)-5-oxo-4,5-dihydro-1H-1,2,4-triazol-3-yl]butyl}piperazin-1-yl)phenyl]acetamide (E40);
N-[3-(4-{2-[4-(Cyclohexylmethyl)-1-methyl-5-oxo-4,5-dihydro-1H-1,2,4-triazol-3-yl]ethyl}piperazino)phenyl]acetamide (E41);
4-(Cyclohexylmethyl)-5-{2-[4-(2-methoxyphenyl)piperazino]ethyl}-2-methyl-2,4-dihydro-3H-1,2,4-triazol-3-one (E42); and
4-(Cyclohexylmethyl)-2-ethyl-5-{2-[4-(2-methoxyphenyl)piperazino]ethyl}-2,4-dihydro-3H-1,2,4-triazol-3-one (E43)

or a pharmaceutically acceptable salt, solvate or hydrate thereof.

In one embodiment, the compounds are selected from E1-E40 or a pharmaceutically acceptable salt, solvate or hydrate thereof.

In one embodiment, the compounds are selected from E10, E17, E21, E37 or E38 or a pharmaceutically acceptable salt, solvate or hydrate thereof.

In a further embodiment, the compounds are selected from E40-E43 or a pharmaceutically acceptable salt, solvate or hydrate thereof. In a yet further embodiment, the compound of formula (I) is the compound of E41 or a pharmaceutically acceptable salt, solvate or hydrate thereof (e.g. N-[3-(4-{2-[4-(Cyclohexylmethyl)-1-methyl-5-oxo-4,5-dihydro-1H-1,2,4-triazol-3-yl]ethyl}piperazino)phenyl]acetamide).

The subject invention also includes isotopically labelled compounds, which are identical to those recited in formula (I) and following, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Examples of such incorporation may be for compounds of formula (I) wherein $R^1$ represents $^{18}F$ or —$OCF_2^{18}F$ or $R^3$ represents —$C_2^{18}F$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography). PET and SPECT are useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labelled reagent.

Methods of Synthesis

It will be appreciated that the compounds of formula (I) may be synthesised via a variety of different routes using commercially available starting materials and/or starting materials prepared by conventional methods.

According to a further aspect of the invention, there is provided a process for preparing a compound of formula (I), which comprises:

(a) preparing a compound of formula (I) wherein $R^1$ represents $C_{1-6}$ alkoxy and $R^3$ represents hydrogen which comprises ring closure of a compound of formula (II):

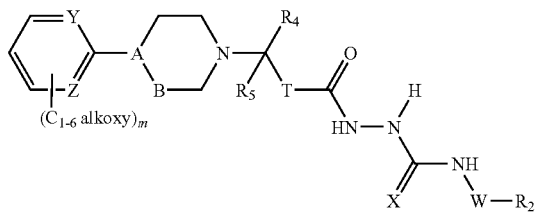

(II)

wherein $R^2$, $R^4$, $R^5$, -A-B—, T, X, Y, Z, W and m are as defined for formula (I)
or:
(b) preparing a compound of formula (I) wherein m represents 1, $R^1$ represents —$NR^6COR^7$ and $R^3$ represents hydrogen which comprises reacting a compound of formula (III):

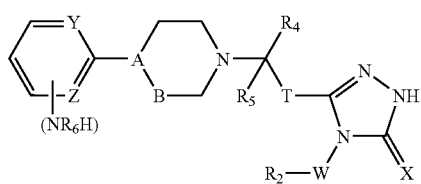

(III)

with a compound of formula $L^1COR^7$,
wherein $L^1$ represents a suitable leaving group such as chlorine, and $R^2$, $R^4$, $R^5$, $R^6$, $R^7$, -A-B—, T, X, Y, Z and W are as defined for formula (I); and optionally thereafter
(c) interconversion of a compound of formula (I) to a further compound of formula (I); and optionally thereafter
(d) deprotection of a protected derivative of formula (I).

Step (a) typically comprises treatment of a compound of formula (II) with a strong alkali (e.g. 2M NaOH).

Step (b) typically comprises acylation of the amine of a compound of formula (III) to form an amide, e.g. using an acid halide, e.g. chlorine, in the presence of pyrimidine.

Step (c) may be performed using conventional interconversion procedures such as epimerisation, oxidation, reduction, alkylation, nucleophilic or electrophilic aromatic substitution, ester hydrolysis, amide bond formation or transition metal mediated coupling reactions. Examples of transition metal mediated coupling reactions useful as interconversion procedures include the following: Palladium catalysed coupling reactions between organic electrophiles, such as aryl halides, and organometallic reagents, for example boronic acids (Suzuki cross-coupling reactions); Palladium catalysed amination and amidation reactions between organic electrophiles, such as aryl halides, and nucleophiles, such as amines and amides; Copper catalysed amidation reactions between organic electrophiles (such as aryl halides) and nucleophiles such as amides; and Copper mediated coupling reactions between phenols and boronic acids.

One example of an interconversion is where compounds of formula (I) wherein $R^3$ represents hydrogen may be converted to compounds of formula (I) wherein $R^3$ represents alkyl, for example using an alkylating agent, such as iodomethane, in the presence of a solvent, e.g. acetonitrile, and a base, e.g. PS-BEMP.

In step (d), examples of protecting groups and the means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxan or trifluoroacetic acid in dichloromethane) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

In one embodiment, compounds of formula (II) may be prepared in accordance with the following Scheme 1, wherein $R^2$, $R^4$, $R^5$, -A-B—, T, X, Y, Z, W and m as defined for formula (I):

Scheme 1

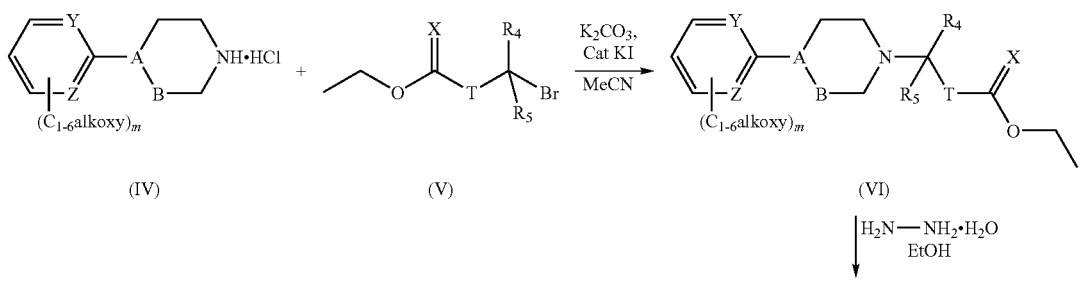

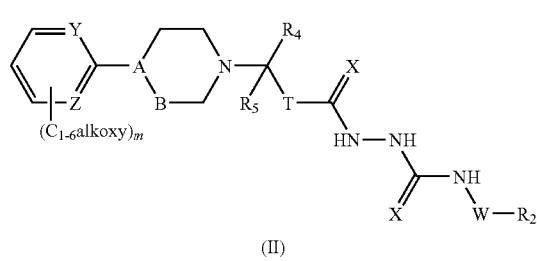

(II)

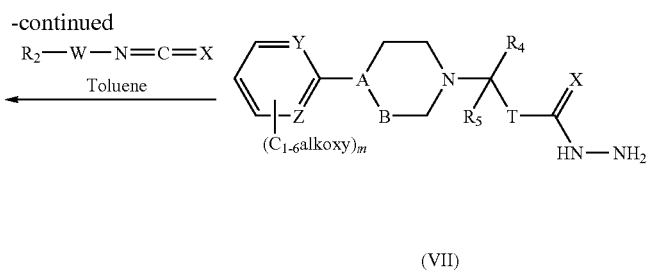

-continued $$R_2\text{—}W\text{—}N\text{=}C\text{=}X \xrightarrow{\text{Toluene}}$$

(VII)

In one embodiment, compounds of formula (III) may be prepared in accordance with the following Scheme 2, wherein $R^2$, $R^4$, $R^5$, -A-B—, T, X, Y, Z and W are as defined for formula (I):

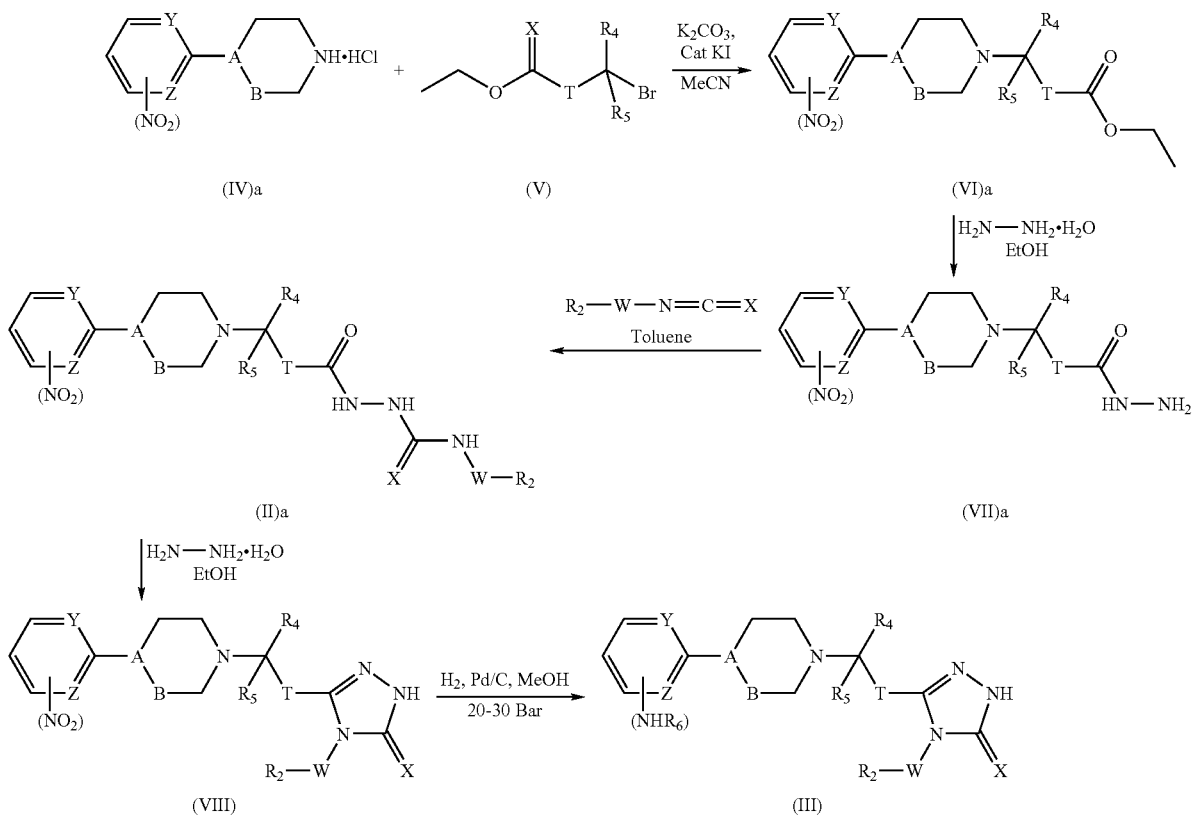

Uses of the Compounds

The compounds according to the invention may be used in therapy, and this is also an embodiment of the invention. Thus, the compounds may be used to treat or prevent a variety of disorders or conditions associated with 5-HT action.

A "disorder or condition associated with 5-HT action" refers to conditions characterised by 5-HT excess or absence, e.g. serotonergic hypofunction or hyperfunction, such as those described in WO 2004/069794, the conditions of which are incorporated herein by reference.

Thus, the compounds of the invention are used to treat diseases, disorders or conditions, including, but not limited to, eating disorders, schizophrenia, neuralgia, and addiction disorders; obsessive compulsive disorders, panic disorders, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, e.g., specific animal phobias, social phobias, stress disorders including post-traumatic stress disorder and acute stress disorder, and generalized anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delirium, dementia, and amnestic and other cognitive or neurodegenerative disorders, such as Alzheimer's disease, senile dementia, dementia of the Alzheimer's type, vascular dementia, and other dementia, for example, due to HIV disease, head trauma, Parkinson's disease, Huntington's disease, Pick's disease, Creutzfeldt-Jakob disease, or due to multiple etiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delirium, withdrawal delirium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and post-therapeutic neuralgia, trigeminal neuralgia, segmental or intercostal neuralgia and other neuralgias; and cerebral vascular disorders due to acute or chronic cerebrovascular damage such as cerebral infarction, subarachnoid hemorrhage or cerebral edema. In an embodiment, conditions characterized by serotonin excess or absence, (serotonergic hypofunction or hyperfunction) do not include depression. The compounds of the invention may also be used in the treatment of obesity and provide a neuroprotective effect against the above mentioned neurodegenerative disorders. The compounds of the invention may further be useful as analgesics in the treatment of pain disorders.

In addition, compounds of the invention may be used for the treatment of vasodilation, smooth muscle contraction, bronchoconstriction, brain disorders such as vascular disorders, e.g, blood flow disorders caused by vasodilation and vasospastic diseases such as angina, vascular headache, migraine and Reynaud's disease; and neuropathological disorders including Parkinson's disease and Alzheimer's disease; modulation of the cardiovascular system; prophylaxis and control of the effects of occurrences of cerebral infarct (Apoplexia cerebri) such as stroke or cerebral ischemia; and for the control of disorders of the intestinal tract which are characterized by disturbances of the serotoninergic system and also by disturbances of the carbohydrate metabolism.

The compounds may also be useful in treating a variety of other conditions including stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

In one embodiment, the compounds are useful in the treatment of cognitive disorders, including schizophrenia, Alzheimer's disease and dementia.

The invention thus provides a method for treating or preventing these diseases or states, the method comprising administering to a patient in need thereof a therapeutically effective amount of the compound of formula (I) without the proviso according to the invention.

It will be appreciated that the term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, and/or to alleviate or relief the symptoms and complications. The patient to be treated is preferably a mammal, in particular a human being, but it may also include animals, such as dogs, cats, cows, sheep and pigs.

In one embodiment, the compounds as described hereinbefore are used to treat or prevent anxiety, more specifically generalised anxiety disorder. In another embodiment, the compound of formula (I) without the proviso is used to treat or prevent depression. In another embodiment, the compound of formula (I) without the proviso is used to treat or prevent panic disorder. In yet another embodiment, the compound of formula (I) without the proviso is used to treat or prevent attention deficit disorder. In yet another embodiment, the compound of formula (I) without the proviso is used to treat or prevent substance-related disorder. In yet another embodiment, the compound of formula (I) without the proviso is used to treat or prevent a vascular disorder.

Thus, in some embodiments, there is provided a use of the compounds of formula (I) without the proviso as hereinbefore defined in the manufacture of a medicament for the treatment or prevention of the diseases, disorders or conditions as hereinbefore described. In a further embodiment, there is provided a pharmaceutical composition comprising a compound of formula (I) without the proviso as hereinbefore defined for use in the treatment of the diseases, disorders or conditions as hereinbefore described.

Combination Therapies

Many diseases are treated using more than one medicament in the treatment, either concomitantly administered or sequentially administered. It is therefore within the scope of the invention to use the compounds of the invention in therapeutic methods for the treatment of one of the above mentioned diseases in combination with one another, or as an adjunct to, or in conjunction with, other established therapies normally used to in the treatment said disease. By analogy, it is also within the scope of the invention to use the compounds of the invention in combination with other therapeutically active compounds normally used in the treatment of one of the above-mentioned diseases in the manufacture of a medicament for said disease.

Examples of such combination therapies may include administration of a compound according to the present invention in combination with a medicament useful for treating anxiety and/or depression such as those disclosed in WO 2004/002858, herein incorporated by reference.

For example, the compounds may be used with other 5-HT agonist/antagonists, and/or selective serotonin reuptake inhibitors (SSRIs) and/or serotonin noradrenaline reuptake inhibitors (SNRIs).

Such combination therapy may also include administration of a compound according to the present invention together with anti-migraine agents, such as those disclosed in WO 2004/002858, herein incorporated by reference.

Such combination therapy may also include administration of a compound according to the present invention together with anti-psychotic agents, such as those disclosed in WO 2004/002858, herein incorporated by reference.

The combination treatment may be carried out in any way as deemed necessary or convenient by the person skilled in the art and for the purpose of this specification, no limitations with regard to the order, amount, repetition or relative amount of the compounds to be used in combination is contemplated.

Pharmaceutical Compositions

Another purpose is to provide a pharmaceutical composition comprising the compounds of the invention. The compounds of the invention may be generally utilised as the free substance or as a pharmaceutically acceptable salt thereof.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water.

In addition, the compounds of the invention may form solvates with water or common organic solvents. Such solvates are also encompassed within the scope of the present invention.

Thus, in a further aspect, there is provided a pharmaceutical composition comprising a compound of formula (I) without the proviso to:

3H-1,2,4-triazole-3-thione, 2,4-dihydro-5-[2-[4-(2-methoxyphenyl)-1-piperazinyl]ethyl]-4-phenyl;

3H-1,2,4-triazole-3-thione, 5-[2-[4-chlorophenyl)-1-piperazinyl]ethyl]-2,4-dihydro-4-phenyl;

3H-1,2,4-triazole-3-thione, 5-[[4-[3-chloro-5-(trifluoromethyl)-2-pyridinyl]-1-piperazinyl]methyl-2,4-dihydro-4-phenyl;

3H-1,2,4-triazole-3-one, 5-[3-[4-(3-chlorophenyl)-1-piperazinyl]propyl]-4-ethyl-2,4-dihydro;

or a pharmaceutically acceptable salt, solvate, or prodrug thereof, and one or more pharmaceutically acceptable carriers, excipients, or diluents.

The composition may further comprise a buffer system, preservative(s), tonicity agent(s), chelating agent(s), stabilizers and surfactants, which is well known to the skilled person. For convenience reference is made to Remington: The Science and Practice of Pharmacy, 20th edition, 2000. The composition may also further comprise one or more therapeutic agents active against the same disease state.

Methods to produce controlled release systems useful for compositions of the current invention include, but are not limited to, crystallization, condensation, co-crystallization, precipitation, co-precipitation, emulsification, dispersion, high pressure homogenisation, en-capsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Composition and Delivery (MacNally, E. J., ed. Marcel Dekker, New York, 2000).

Administration of pharmaceutical compositions according to the invention may be through several routes of administration, for example, oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

For topical use, sprays, creams, ointments, jellies, gels, inhalants, dermal patches, implants, solutions of suspensions, etc., containing the compounds of the present invention are contemplated. For the purpose of this application, topical applications shall include mouth washes and gargles.

Pharmaceutical compositions for oral administration include solid dosage forms such as hard or soft capsules, tablets, troches, dragees, pills, lozenges, powders and granules and liquid dosage forms for oral administration include solutions, emulsions, aqueous or oily suspensions, syrups and elixirs, each containing a predetermined amount of the active ingredient, and which may include a suitable excipient.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations.

Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265, 874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as a solvent or suspending medium. For this purpose, any bland fixed oil may be employed using synthetic mono- or diglycerides. In addition, fatty acids such as oleic acid find use in the preparation of injectables.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the prolactin receptor antagonist in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use.

The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Depot injectable formulations are also contemplated as being within the scope of the present invention.

When the compounds of the invention or composition thereof is used in combination with a second therapeutic agent active against the same disease state, they may conveniently be administered alone or in combination, in either single or multiple doses, sequentially or simultaneously, by the same route of administration, or by a different route.

Effective Dosages

The compounds of the invention, or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the systems associated with the underlying disorder. Therapeutic benefit also includes halting or slowing the progression of the disease, regardless of whether improvement is realised.

The exact dosage will depend upon the frequency and mode of administration, the sex, age, weight and general condition of the subject treated, the nature and severity of the condition treated and any concomitant diseases to be treated and other factors evident to those skilled in the art. Determination of the effective dosage is well within the capabilities of those skilled in the art.

When a compound of the invention or a pharmaceutically acceptable salt, solvate or prodrug thereof is used in combination with a second therapeutic agent active against the same disease state the dose of each compound may differ from that when the compound is used alone. Appropriate doses will be readily appreciated by those skilled in the art.

EXAMPLES

The invention will be further defined by reference to the following examples, which describe the preparation of the various compounds described herein and methods for assaying their biological activity. It will be apparent to those skilled in the art that many modifications, both to the materials and methods may be practiced without departing from the scope of the invention.

General LC-MS Analytical Method

LC-Phenomenex Gemini 5µ, 50×4.6 mm, 40° C., 1 mL/min, 20-90% CH$_3$CN in H$_2$O (+0.1% ammonium acetate), 0.5 min hold, 3.5 min gradient—held for 1 min, DAD before re-equilibration at 20% CH$_3$CN, 200-300 nm, 7 min run, injection volume 1-5 µL. MS-APCI+ve mode, mass range 300-800, scan speed 500.

Intermediates

Intermediate 1

Ethyl 3-[4-(2-methoxyphenyl)piperazino]propanoate (D1)

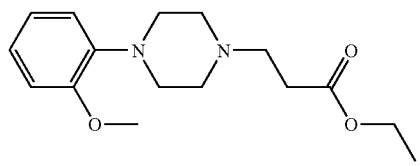

A mixture of 1-(2-methoxyphenyl)piperazine hydrochloride (9.10 g, 39.78 mmol), ethyl 3-bromopropionate (7.29 g, 5.14 mL, 40.29 mmol), potassium carbonate (20.00 g, 144.70 mmol) and a catalytic amount of potassium iodide in acetonitrile (80 mL) was heated at reflux for 18 hrs. After cooling at room temperature the solvent was evaporated under reduced pressure and the residue was taken up in dichloromethane. The organic phase was washed with water, dried over MgSO$_4$ and evaporated to dryness. The resulting orange oil was purified by flash chromatography (Silica gel 60 Å, 45 µm, 50% ethyl acetate in hexane) and afforded 8.30 g (71%) ethyl 3-[4-(2-methoxyphenyl)piperazino]propanoate D1 as an oil.

$^1$H NMR (400 MHz, CDCl$_3$): δ$_H$ 7.03-6.83 (4H, m, aryl), 4.13 (2H, q, J 7.1 Hz, OCH$_2$), 3.85 (3H, s, OCH$_3$), 3.09 (4H, br., NCH$_2$), 2.76 (2H, t, J 7.4 Hz, NCH$_2$CH$_2$CO), 2.66 (4H, br., CH$_2$N), 2.52 (2H, t, J 7.4 Hz, NCH$_2$CH$_2$CO), 1.24 (3H, t, J 7.1 Hz, CH$_2$CH$_3$).

Intermediate 2

3-[4-(2-Methoxyphenyl)piperazino]propanohydrazide (D2)

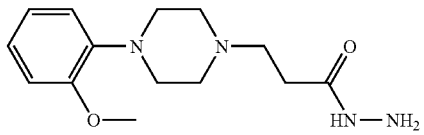

A solution of ethyl 3-[4-(2-methoxyphenyl)piperazino] propanoate D1 (8.30 g, 28.38 mmol) and hydrazine monohydrate (8.52 g, 8.3 mL, 170.03 mmol) in ethanol (80 mL) was refluxed for 18 hrs. The solvent was evaporated under reduced pressure, the resulting solid was slurred in 50% acetone in hexane, filtered and dried to afford 6.80 g (87%) 3-[4-(2-methoxyphenyl)piperazino]propanohydrazide D2 as a white solid.

$^1$H NMR (400 MHz, CDCl$_3$): δ$_H$ 9.28 (1H, br. s, NH), 7.05-6.95 (1H, m, aryl), 6.94-6.83 (3H, m, aryl), 4.10-3.70 (5H, br. and s, NH$_2$ and OCH$_3$), 3.30-3.00 (4H, br., NCH$_2$), 2.85-2.60 (6H, m, CH$_2$N and NCH$_2$CH$_2$CO), 2.50 (2H, t, J 6.1 Hz, NCH$_2$CH$_2$CO).

LC-MS: Retention time 2.1 min, 100%, ES$^+$: 279 [MH]$^+$

Intermediate 3

N-Cyclooctyl-2-{3-[4-(2-methoxyphenyl)piperazino]propanoyl}-1-hydrazinecarboxamide (D3)

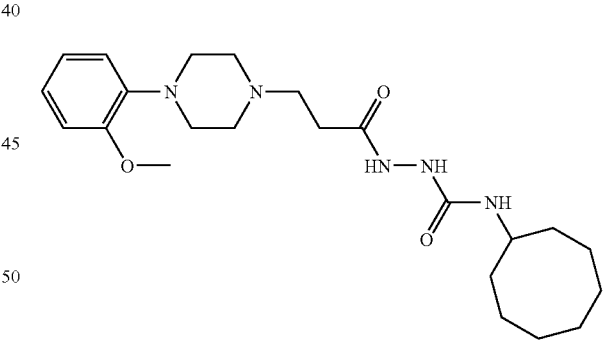

To a suspension of 3-[4-(2-methoxyphenyl)piperazino] propanohydrazide D2 (0.30 g, 1.07 mmol) in anhydrous toluene (5 mL), cyclooctyl isocyanate (0.177 g, 1.15 mmol) was added and the mixture was heated at reflux until all solid dissolved. The solution was allowed to cool slowly to room temperature. Hexane was added and the resulting oil was extracted with ethyl acetate, the organic phase was washed with water, dried over MgSO$_4$ and evaporated under reduced pressure to afford 0.40 g (84%) N-cyclooctyl-2-{3-[4-(2-methoxyphenyl)piperazino]propanoyl}-1-hydrazine-carboxamide D3 as a colourless oil.

$^1$H NMR (400 MHz, DMSO-d6): δ$_H$ 9.52 (1H, br., NH), 7.59 (1H, br., NH), 6.98-6.82 (4H, m, aryl), 6.01 (1H, br., N H), 3.76 (3H, s, OCH$_3$), 3.70-3.58 (1H, m), 3.00-2.90 (4H, br., NCH$_2$), 2.65-2.50 (8H, m), 1.75-1.40 (14H, m).

Intermediate 4

N-(Cyclohexylmethyl)-2-{3-[4-(2-methoxyphenyl)piperazino]propanoyl}-1-hydrazinecarboxamide (D4)

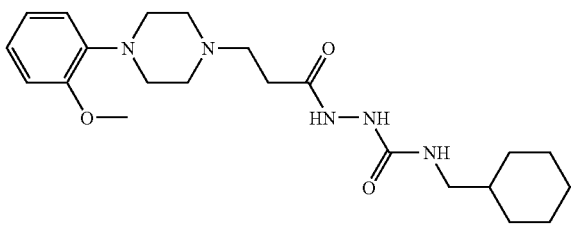

To a suspension of 3-[4-(2-methoxyphenyl)piperazino]propanohydrazide D2 (0.30 g, 1.07 mmol) in anhydrous toluene (5 mL), cyclohexanemethyl isocyanate (0.16 g, 0.165 mL, 1.16 mmol) was added and the mixture was heated at reflux until all solid dissolved. The solution was allowed to cool slowly to room temperature. Hexane was added and the resulting oil was extracted with ethyl acetate, the organic phase was washed with water, dried over MgSO$_4$ and evaporated under reduced pressure to afford 0.40 mg (87%) N-(cyclohexylmethyl)-2-{3-[4-(2-methoxyphenyl)piperazino]propanoyl}-1-hydrazinecarboxamide D4 as a pale yellow oil.

$^1$H NMR (400 MHz, DMSO-d6): $\delta_H$ 9.52 (1H, br., NH), 7.66 (1H, br., NH), 7.00-6.86 (4H, m, aryl), 6.17 (1H, br., NH), 3.77 (3H, s, OCH$_3$), 3.00-2.92 (4H, br., NCH$_2$), 2.90-2.83 (2H, m), 2.60-2.53 (2H, m), 2.32-2.25 (5H, m), 1.70-1.55 (6H, m), 1.40-1.30 (1H, m), 1.20-1.05 (3H, m), 0.90-0.72 (2H, m)

Intermediate 5

2-{3-[4-(2-Methoxyphenyl)piperazino]propanoyl}-N-phenyl-1-hydrazinecarboxamide (D5)

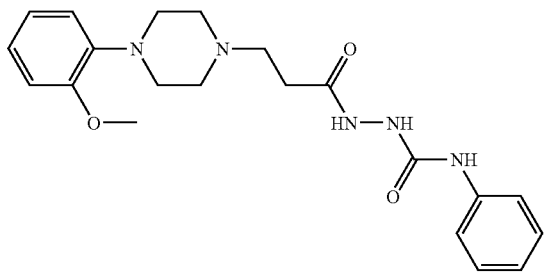

To a suspension of 3-[4-(2-methoxyphenyl)piperazino]propanohydrazide D2 (1.00 g, 3.60 mmol) in anhydrous toluene (2 mL), phenyl isocyanate (0.45 g, 0.41 mL, 3.78 mmol) was added and the mixture was stirred at room temperature for 30 min and then heated at reflux for 1 h. The solution was allowed to cool slowly to room temperature and the resulting precipitate was filtered and washed with hexane to afford 1.2 g (83.9%) 2-{3-[4-(2-methoxyphenyl)piperazino]propanoyl}-N-phenyl-1-hydrazinecarboxamide D5 as a white solid.

$^1$H NMR (400 MHz, DMSO-d6): $\delta_3$, 9.56 (1H, br., NH), 7.68 (1H, br., NH), 7.60-7.40 (5H, m, aryl), 7.00-6.80 (4H, m, aryl), 6.19 (1H, br., NH), 3.76 (3H, s, OCH$_3$), 2.90-2.80 (4H, br., NCH$_2$), 2.65-2.54 (2H, m), 2.54-2.32 (6H, m)

Intermediate 6

Ethyl 3-[4-(3-nitrophenyl)piperazino]propanoate (D6)

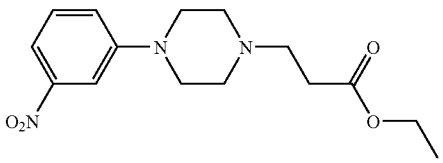

A mixture of 1-(3-nitrophenyl)piperazine hydrochloride (2.6 g, 10.66 mmol), ethyl 3-bromopropionate (2.41 g, 1.7 mL, 13.32 mmol), potassium carbonate (6.1 g, 44.13 mmol) and a catalytic amount of potassium iodide in acetonitrile (30 mL) was heated at reflux for 18 hrs. After cooling to room temperature the solvent was evaporated under reduced pressure and the residue was taken up in dichloromethane. The organic phase was washed with water, dried over MgSO$_4$ and evaporated to dryness to afford 3.00 g (91.5%) ethyl 3-[4-(3-nitrophenyl)piperazino]propanoate D6 as an orange oil which crystallised on standing.

$^1$H NMR (400 MHz, CDCl$_3$): $\delta_H$ 7.72-7.60 (2H, m, aryl), 7.40-7.32 (1H, m, aryl), 7.20-7.13 (1H, m, aryl), 4.14 (2H, q, J 7.1 Hz, CH$_2$CH$_3$), 3.30-3.20 (4H, m), 2.75 (2H, t, J 7.3 Hz, NCH$_2$CH$_2$CO), 2.65-2.60 (4H, m), 2.52 (2H, t, J 7.3 Hz, NCH$_2$CH$_2$CO), 1.25 (3H, t, J 7.1 Hz, CH$_2$CH$_3$).

Intermediate 7

3-[4-(3-Nitrophenyl)piperazino]propanohydrazide (D7)

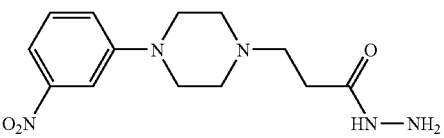

A solution of ethyl 3-[4-(3-nitrophenyl)piperazino]propanoate D6 (3.00 g, 9.76 mmol) and hydrazine monohydrate (2.93 g, 2.85 mL, 58.56 mmol) in ethanol (30 mL) was refluxed for 24 hrs. The solvent was evaporated under reduced pressure, brine was added to the residue and the product was extracted several times with dichloromethane. The combined organic phases were dried over MgSO$_4$ and the solvent was evaporated under reduced pressure to afford 3.00 g crude product as an orange semi-solid. Purification by flash chromatography (Silica gel 60 Å, 45 µm, 10% methanol in dichloromethane) afforded 0.55 g (19%) 3-[4-(3-nitrophenyl)piperazino]propanohydrazide D7.

$^1$H NMR (400 MHz, DMSO-d6): $\delta_H$ 8.97 (1H, br., NH), 7.75-7.60 (2H, m, aryl), 7.44-7.32 (1H, m, aryl), 7.28-7.18

(1H, m, aryl), 4.14 (2H, br., NH$_2$) 3.35-3.20 (4H, m), 2.59 (2H, t, J 7.3 Hz, NCH$_2$CH$_2$CO), 2.55-2.48 (4H, m), 2.24 (2H, t, J 7.3 Hz, NCH$_2$CH$_2$CO).

Intermediate 8

N-(Cyclohexylmethyl)-2-{3-[4-(3-nitrophenyl)piperazin-1-yl]propanoyl}hydrazine carboxamide (D8)

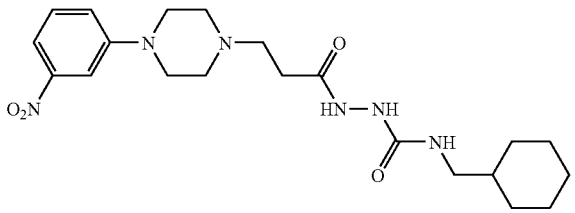

A solution of 3-[4-(3-nitrophenyl)piperazino]propanohydrazide D7 (0.55 g, 1.87 mmol) in toluene (30 mL) was heated at 70° C. and cyclohexanemethyl isocyanate (0.28 g, 0.30 mL, 1.96 mmol) was added at once. The slurry was heated at 70° C. until all solid went into solution (15 min) and then cooled to room temperature. The resulting solid was filtered and washed with toluene to afford 0.70 g (95%) N-(cyclohexylmethyl)-2-{3-[4-(3-nitrophenyl)piperazin-1-yl] propanoyl}hydrazine carboxamide D8 as an orange semi-solid.

$^1$H NMR (400 MHz, DMSO-d6): δ$_H$ 9.52 (1H, br., NH), 7.67-7.63 (2H, m, aryl), 7.60-7.55 (1H, m, aryl), 7.50-7.39 (2H, m, NH and aryl), 6.14 (1H, br., NH), 3.28-3.25 (4H, br., NCH$_2$), 2.84 (2H, t, J 6.4 Hz, NCH$_2$CH$_2$CO), 2.65-2.53 (6H, m, CH$_2$N and NCH$_2$CH$_2$CO), 2.35-2.28 (2H, m), 1.68-1.52 (5H, m), 1.37-1.24 (1H, m), 1.17-1.00 (3H, m), 0.87-0.72 (2H, m).

Intermediate 9

4-(Cyclohexylmethyl)-5-{2-[4-(3-nitrophenyl)piperazin-1-yl]ethyl}-2,4-dihydro-3H-1,2,4-triazol-3-one (D9)

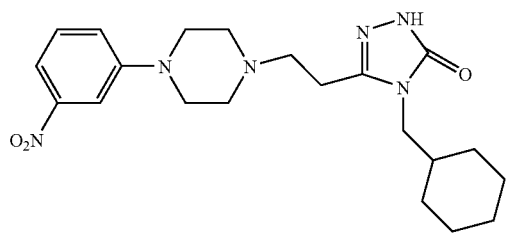

A suspension of N-(cyclohexylmethyl)-2-{3-[4-(3-nitrophenyl)piperazin-1-yl]propanoyl}hydrazine carboxamide D8 (0.70 g, 1.62 mmol) in 2M NaOH aqueous solution (10 mL) was heated at reflux for 5 hrs, then cooled to room temperature and brought to pH 8 by the drop-wise addition of HCl 28%. The resulting precipitate was filtered, washed with water and diethyl ether to afford 0.60 g (89%) 4-(cyclohexylmethyl)-5-{2-[4-(3-nitrophenyl)piperazin-1-yl]ethyl}-2,4-dihydro-3H-1,2,4-triazol-3-one D9 as a yellow solid.

$^1$H NMR (400 MHz, DMSO-d6): δ$_H$ 11.60-11.04 (1H, br., NH), 7.68-7.37 (4H, m, aryl), 3.39 (2H, d, J 7.4 Hz, NCH$_2$CH-cyclohexyl), 3.29-3.24 (4H, br., NCH$_2$), 2.72-2.68 (4H, br.), 2.62-2.57 (4H, br., CH$_2$N), 1.72-1.50 (6H, m), 1.22-1.08 (3H, m), 1.01-0.89 (2H, m).

Intermediate 10

5-{2-[4-(3-Aminophenyl)piperazin-1-yl]ethyl}-4-(cyclohexylmethyl)-2,4-dihydro-3H-1,2,4-triazol-3-one (D10)

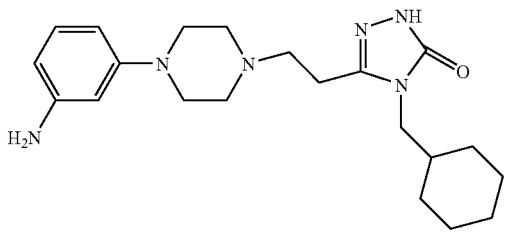

To a solution of 4-(cyclohexylmethyl)-5-{2-[4-(3-nitrophenyl)piperazin-1-yl]ethyl}-2,4-dihydro-3H-1,2,4-triazol-3-one D9 (0.30 g, 0.72 mmol) in methanol (20 mL), a catalytic amount of 10% Pd/C was added and the slurry was pressurized to 20-30 bar in an autoclave for 3 days. The catalyst was filtered through a Celite pad and the filtrate was evaporated to afford 0.26 g (93%) 5-{2-[4-(3-aminophenyl)piperazin-1-yl]ethyl}-4-(cyclohexylmethyl)-2,4-dihydro-3H-1,2,4-triazol-3-one D10 as an orange semi-solid.

LC-MS: Retention time 3.13 min, 80%, ES$^+$: 385 [MH]$^+$

Intermediate 11

Ethyl 3-[4-(2-methoxyphenyl)piperazin-1-yl]butanoate (D11)

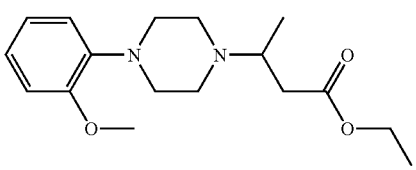

A slurry of 1-(2-methoxyphenyl)piperazine hydrochloride (5 g, 21.86 mmol), ethyl 3-bromobutyrate (4.48 g, 22.96 mmol), potassium carbonate (10.57 g, 76.51 mmol) and a catalytic amount of potassium iodide (0.362 g, 2.18 mmol) in acetonitrile (50 mL) was heated at reflux for 18 hrs. After cooling at room temperature, the reaction mixture was added to water (100 mL) and the aqueous phase was extracted with AcOEt (100 mL). The organic phase was washed with water (2×75 mL), brine (75 mL), dried over MgSO$_4$ and evaporated to dryness. The resulting light yellow oil was purified by flash chromatography (Biotage Isolute SI, 40 g column, gradient hexane to 33% ethyl acetate in hexane) and afforded 2.8 g (42%) ethyl 3-[4-(2-methoxyphenyl)piperazin-1-yl]butanoate D11 as a colourless oil.

$^1$H NMR (400 MHz, CDCl$_3$): δ$_H$ 7.02-6.82 (4H, m, aryl), 4.20-4.10 (2H, m, OCH$_2$), 3.85 (3H, s, OCH$_3$), 3.28-3.18 (1H, m), 3.09 (4H, br., NCH$_2$), 2.80-2.68 (4H, br., CH$_2$N), 2.67-2.57 (1H, m), 2.31-2.22 (1H, m), 1.30-1.20 (3H, m, CH$_2$CH$_3$), 1.11 (3H, d, J 6.6 Hz, CH$_3$CH).
LC-MS: Retention time 4.30 min, 100%, ES$^+$: 307 [MH]$^+$ Intermediate 12

3-[4-(2-Methoxyphenyl)piperazin-1-yl]butanohydrazide (D12)

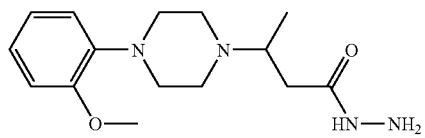

A solution of ethyl 3-[4-(2-methoxyphenyl)piperazin-1-yl]butanoate D11 (2.75 g, 8.97 mmol) and hydrazine monohydrate (2.7 g, 53.85 mmol) in ethanol (40 mL) was refluxed for 48 hrs. The solvent was evaporated under reduced pressure, toluene (50 mL) was added and the solvent was evaporated and the resulting light yellow oil was triturated with 50% AcOEt in hexane (10 mL). The resulting white solid was filtered, washed with hexane and dried to afford 2 g (76%) 3-[4-(2-methoxyphenyl)piperazin-1-yl]butanohydrazide D12.

$^1$H NMR (400 MHz, CDCl$_3$): δ$_H$ 9.52 (1H, br. s, NH), 7.05-6.80 (4H, m, aryl), 4.10-3.60 (5H, br. and s, NH$_2$ and OCH$_3$), 3.41-3.30 (1H, m), 3.28-3.01 (4H, br., NCH$_2$), 2.98-2.88 (2H, br.), 2.81-2.70 (2H, br.), 2.68-2.52 (1H, m), 2.35-2.28 (1H, m), 1.12 (3H, d, J 6.6 Hz, CH$_3$CH).
LC-MS: Retention time 2.44 min, 100%, ES$^+$: 293 [MH]$^+$ Intermediate 13

N-(Cyclohexylmethyl)-2-{3-[4-(2-methoxyphenyl)piperazin-1-yl]butanoyl}hydrazinecarboxamide (D13)

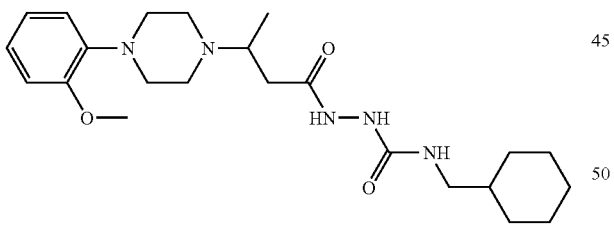

To a suspension of 3-[4-(2-methoxyphenyl)piperazin-1-yl]butanohydrazide D12 (0.5 g, 1.71 mmol) in anhydrous toluene (7 mL), cyclohexanemethyl isocyanate (0.25 g, 1.80 mmol) was added dropwise at room temperature, the mixture was heated at 100° C. and stirred for 10 min. The solution was allowed to cool slowly to room temperature, AcOEt (15 mL) was added and the organic phase was washed with water (2×10 mL), dried over MgSO$_4$ and evaporated under reduced pressure to afford 0.909 g N-(cyclohexylmethyl)-2-{3-[4-(2-methoxyphenyl)piperazin-1-yl]butanoyl}hydrazinecarboxamide D13 as an orange oil. The product containing little toluene was used in the next step without further purification.
LC-MS: Retention time 3.61 min, 96%, ES$^+$: 432 [MH]$^+$ Intermediate 14

4-(Cyclohexylmethyl)-5-{2-[4-(2-methoxyphenyl)piperazin-1-yl]propyl}-2,4-dihydro-3H-1,2,4-triazol-3-one (D14)

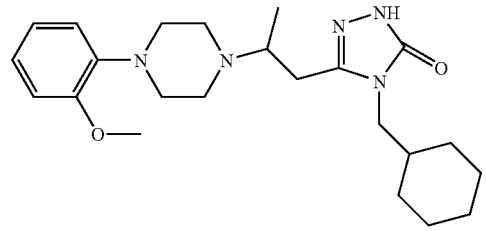

N-(Cyclohexylmethyl)-2-{3-[4-(2-methoxyphenyl)piperazin-1-yl]butanoyl}hydrazinecarboxamide D13 (0.90 g, 2.08 mmol) in 2M NaOH aqueous solution (20 mL) was heated at reflux for 18 hrs. The pH was adjusted to 8 with conc. HCl and the resulting yellow slurry was extracted twice with DCM (50 mL and 20 mL). The combined organic extracts were filtered and DCM evaporated under reduced pressure to a light yellow glassy solid. Purification by flash chromatography (Silica gel 60 Å, 45 μm 10% methanol in dichloromethane) afforded 0.42 g (48.8%) 4-(cyclohexylmethyl)-5-{2-[4-(2-methoxyphenyl)piperazin-1-yl]propyl}-2,4-dihydro-3H-1,2,4-triazol-3-one D14 as a cream solid.

$^1$H NMR (400 MHz, CDCl$_3$): δ$_H$ 9.58 (1H, br. s, NH), 7.05-6.82 (4H, m, aryl), 3.88 (3H, s, OCH$_3$), 3.48 (2H, d, J 7.2 Hz, NCH$_2$cyclohexyl), 3.22-305 (5H, m and br.), 2.90-2.75 (5H, m and br.), 2.48-2.40 (1H, m), 1.80-1.60 (6H, m, CH$_{cyclohexyl}$), 1.25-1.10 (6H, m, CH$_{cyclohexyl}$ and CH$_3$CH), 1.06-0.85 (2H, m, CH$_{cyclohexyl}$).
LC-MS: Retention time 3.98 min, 70%, ES$^+$: 414 [MH]$^+$ Intermediate 15

4-(Cyclohexylmethyl)-2-methyl-5-{2-[4-(3-nitrophenyl)piperazino]ethyl}-2,4-dihydro-3H-1,2,4-triazol-3-one (D15)

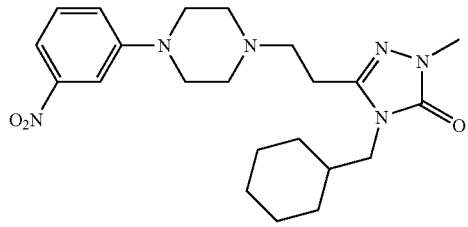

To a mixture of 4-(cyclohexylmethyl)-5-{2-[4-(3-nitrophenyl)piperazin-1-yl]ethyl}-2,4-dihydro-3H-1,2,4-triazol-3-one (D9; 500 mg, 1.207 mmol) and NaH (60% in mineral oil, 97 mg, 2.412 mmol), DMF (20 mL) was added and the slurry was stirred at room temperature for 10 min. Methyl iodide (0.226 mL, 3.621 mmol) was added and the reaction mixture was stirred at room temperature for 2.5 hrs. The reaction was quenched with water (3 mL) and the solvents were removed in vacuo. The resulting yellow solid was triturated with 10% MeOH in AcOEt (250 mL) and the solid filtered. The filtrate was evaporated to afford 1.3 g crude yellow solid which was further purified by flash chromatography (Flash Master, Biotage Isolute SI, 5 g column, gradient AcOEt for 3 min, then 0-10% MeOH in AcOEt for 27 min and 10% MeOH in AcOEt for 15 min) to afford 490 mg (94%) of the title compound as an orange solid.

LC-MS: Retention time 6.38 min, 98.45%, ES$^+$: 429 [MH]$^+$

Intermediate 16

5-{2-[4-(3-aminophenyl)piperazino]ethyl}-4-(cyclohexyl methyl)-2-methyl-2,4-dihydro-3H-1,2,4-triazol-3-one (D16)

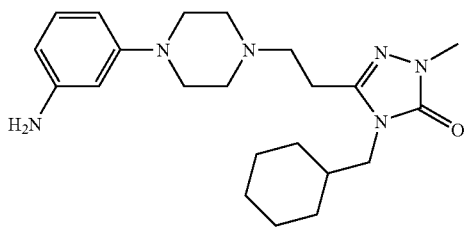

A slurry of 4-(cyclohexylmethyl)-2-methyl-5-{2-[4-(3-nitrophenyl)piperazino]ethyl}-2,4-dihydro-3H-1,2,4-triazol-3-one (D15; 490 mg, 1.143 mmol) and 10% Pd/C (250 mg) in MeOH (30 mL) was hydrogenated in an autoclave at 30 bar and room temperature for 4 hrs. The reaction mixture was filtered over a pad of Celite and the solvent was removed in vacuo to afford a light-brown film. This was re-dissolved in MeCN (20 mL) and filtered again through a Celite plug. The solvent was evaporated in vacuo to afford 450 mg (99%) of the title compound as a brown solid.

LC-MS: Retention time 4.75 min, 100%, ES$^+$: 399 [MH]$^+$

Example 1

4-Ethyl-5-{2-[4-(2-methoxyphenyl)piperazino]ethyl}-2,4-dihydro-3H-1,2,4-triazol-3-one (E1)

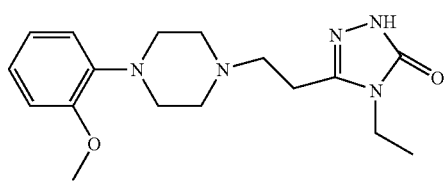

E1 may be prepared in an analogous manner to E2, E10 and E17.

Example 2

5-{2-[4-(2-Methoxyphenyl)piperazino]ethyl}-4-phenyl-2,4-dihydro-3H-1,2,4-triazol-3-one (E2)

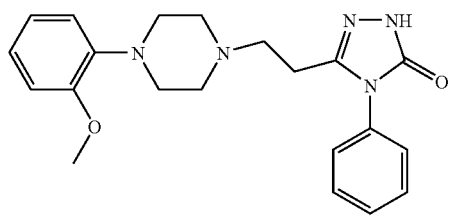

A suspension of 2-{3-[4-(2-methoxyphenyl)piperazino]propanoyl}-N-phenyl-1-hydrazine carboxamide D5 (1.00 g, 2.50 mmol) in 2M NaOH aqueous solution (10 mL) was heated at reflux for 5 hrs. The pH of the solution was adjusted to 8 by the sequential addition of HCl 28% and NaOH, and the resulting white precipitate was filtered, washed with water and diethyl ether to afford 0.80 g (84%) 5-{2-[4-(2-methoxyphenyl)piperazino]ethyl}-4-phenyl-2,4-dihydro-3H-1,2,4-triazol-3-one E2.

$^1$H NMR (400 MHz, DMSO-d6): $\delta_H$ 11.65 (1H, br., NH), 7.61-7.40 (5H, m, aryl), 6.96-6.80 (4H, m, aryl), 3.76 (3H, s, OCH$_3$), 2.90-2.80 (4H, br., NCH$_2$), 2.65-2.54 (2H, m), 2.54-2.32 (6H, m)

LC-MS: Retention time 3.39 min, 100%, ES$^+$: 380 [MH]$^+$

Examples 3-9

E3-E9 may be prepared in an analogous manner to E2, E10 and E17.

Example 3

2-Ethyl-5-{2-[4-(2-methoxy-phenyl)-piperazin-1-yl]-ethyl}-4-phenyl-2,4-dihydro-[1,2,4]triazol-3-one (E3)

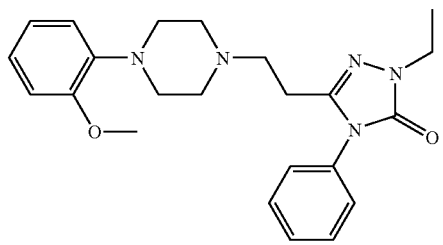

$^1$H NMR (400 MHz, CDCl$_3$): $\delta_H$ 7.55-7.40 (3H, m, aryl), 7.40-7.30 (2H, m, aryl), 7.05-6.97 (1H, m, aryl), 6.95 (3H, m, aryl), 3.95-3.80 (5H, m, CH$_2$ and OCH3), 3.50-2.50 (12H, 2×br., CH$_2$), 1.38 (3H, t, J 8 Hz, CH$_3$).

LC-MS: Retention time 3.87 min, 100%, ES$^+$: 408 [MH]$^+$

Example 4

2-Isopropyl-5-{2-[4-(2-methoxy-phenyl)-piperazin-1-yl]-ethyl}-4-phenyl-2,4-dihydro-[1,2,4]triazol-3-one (E4)

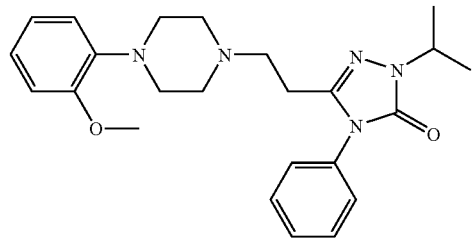

¹H NMR (400 MHz, CDCl₃): δ$_H$ 7.50-7.35 (3H, m, aryl), 7.30 (2H, d, J 1.6 Hz, aryl), 7.00-6.92 (1H, m, aryl), 6.90-6.79 (3H, m, aryl), 4.50 (1H, m, CH₃CHCH₃), 3.8 (3H, s, OCH₃), 3.11-2.90 (4H, br., NCH₂), 2.72-2.45 (8H, m), 1.38 (6H, d, J 6.7 Hz, CH₃CHCH₃).

LC-MS: Retention time 4.17 min, 100%, ES⁺: 422 [MH]⁺

Example 5

4-(4-Methoxy-phenyl)-5-{2-[4-(2-methoxy-phenyl)-piperazin-1-yl]-ethyl}-2,4-dihydro-[1,2,4]triazol-3-one (E5)

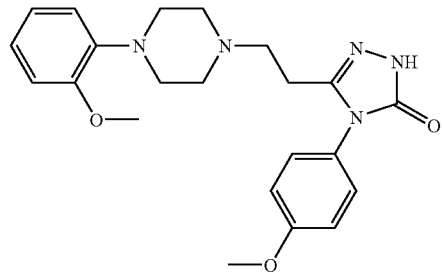

¹H NMR (400 MHz, DMSO-d6): δ$_H$ 11.58 (1H, br. s, NH), 7.32 (2H, d, J 8 Hz, aryl), 7.08 (2H, d, J 8 Hz, aryl), 6.95-6.80 (4H, m, aryl), 3.83 (3H, s, OCH₃), 3.78 (3H, s, OCH₃), 2.92-2.80 (4H, br., NCH₂), 2.60-2.35 (8H, m).

LC-MS: Retention time 3.47 min, 100%, ES⁺: 410 [MH]⁺

Example 6

4-(4-Chloro-phenyl)-5-{2-[4-(2-methoxy-phenyl)-piperazin-1-yl]-ethyl}-2,4-dihydro-[1,2,4]triazol-3-one (E6)

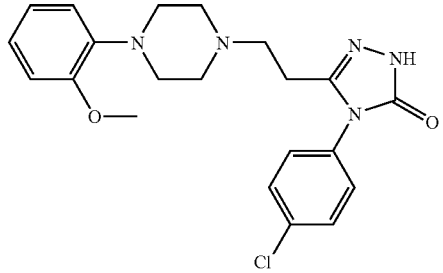

¹H NMR (400 MHz, DMSO-d6): δ$_H$ 11.68 (1H, br., NH), 7.61 (2H, d, J 8.7 Hz, aryl), 7.47 (2H, d, J 8.2 Hz, aryl), 7.00-6.80 (4H, m, aryl), 3.75 (3H, s, OCH₃), 3.00-2.80 (8H, m), 2.68-2.60 (2H, m, CH₂), 2.55-2.45 (obscured by DMSO), 2.45-2.35 (4H, br.).

LC-MS: Retention time 3.76 min, 100%, ES⁺: 414 [MH]⁺

Example 7

4-Cyclopentyl-5-{2-[4-(2-methoxy-phenyl)-piperazin-1-yl]-ethyl}-2,4-dihydro-[1,2,4]triazol-3-one (E7)

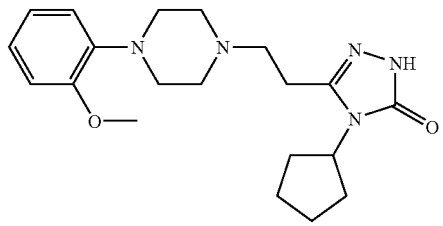

¹H NMR (400 MHz, DMSO-d6): δ$_H$ 11.34 (1H, br., NH), 7.00-6.83 (4H, m, aryl), 4.28 (1H, m, cyclopentyl), 3.80 (3H, s, OCH₃), 3.10-2.90 (4H, br., NCH₂), 2.90-2.60 (8H, br., NCH₂ and CH₂), 2.15-2.00 (2H, m), 1.90-1.75 (4H, m), 2.60-2.50 (2H, m).

LC-MS: Retention time 3.50 min, 100%, ES⁺: 372 [MH]⁺

Example 8

4-Cyclohexyl-5-{2-[4-(2-methoxy-phenyl)-piperazin-1-yl]-ethyl}-2,4-dihydro-[1,2,4]triazol-3-one (E8)

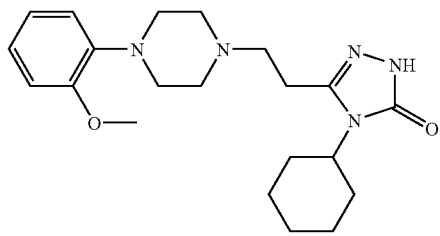

$^1$H NMR (400 MHz, DMSO-d6): $\delta_H$ 11.45 (1H, br. s, NH), 7.10-6.85 (4H, m, aryl), 3.85-3.70 (4H, m, OCH$_3$ and NCH), 3.30-2.80 (12H, br., CH$_2$), 2.20-2.00 (2H, m, CH$_2$), 1.85-1.60 (5H, m, CH$_2$), 1.40-1.25 (2H, m, CH$_2$), 1.20-1.08 (1H, m, CH$_2$).

LC-MS: Retention time 3.67 min, 97%, ES$^+$: 386 [MH]$^+$

Example 9

4-Cycloheptyl-5-{2-[4-(2-methoxy-phenyl)-piperazin-1-yl]-ethyl}-2,4-dihydro-[1,2,4]triazol-3-one (E9)

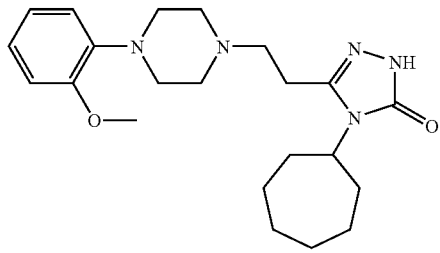

$^1$H NMR (400 MHz, DMSO-d6): $\delta_H$ 11.28 (1H, br. s, NH), 7.00-6.85 (4H, m, aryl), 3.95-3.82 (1H, m, NCH), 3.78 (3H, s, OCH$_3$), 3.00-2.92 (4H, br., NCH$_2$), 2.78-2.55 (8H, m, CH$_2$), 2.22-2.10 (2H, m, CH$_2$), 1.82-1.70 (4H, m, CH$_2$), 1.70-1.40 (6H, m, CH$_2$).

LC-MS: Retention time 3.85 min, 100%, ES$^+$: 400 [MH]$^+$

Example 10

4-Cyclooctyl-5-{2-[4-(2-methoxyphenyl)piperazino]ethyl}-2,4-dihydro-3H-1,2,4-triazol-3-one (E10)

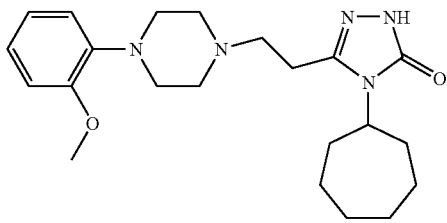

A suspension of N-cyclooctyl-2-{3-[4-(2-methoxyphenyl)piperazino]propanoyl}-1-hydrazinecarboxamide D3 (0.40 g, 0.93 mmol) in 2M NaOH aqueous solution (10 mL) was heated at reflux for 18 hrs. The solution was cooled to room temperature and the pH was adjusted to 8 by the drop-wise addition of HCl 28%. The resulting precipitate was filtered to afford a white solid, which was twice boiled with ethyl acetate and filtered while hot. The filtrates were combined and evaporated under reduced pressure to afford 0.18 g (47%) 4-cyclooctyl-5-{2-[4-(2-methoxyphenyl)piperazino]ethyl}-2,4-dihydro-3H-1,2,4-triazol-3-one E10.

$^1$H NMR (400 MHz, DMSO-d6): $\delta_H$ 11.28 (1H, br. s, NH), 7.00-6.80 (4H, m, aryl), 4.00-3.90 (1H, m, NCH-cyclooctyl), 3.80 (3H, s, OCH$_3$), 3.02-2.90 (4H, br., NCH$_2$), 2.75-2.50 (7H, m), 2.28-2.21 (2H, m), 1.80-1.41 (13H, m).

LC-MS: Retention time 4.07 min, 100%, ES$^+$: 414 [MH]$^+$

Examples 11-16

E11-E16 may be prepared in an analogous manner to E2, E10 and E17.

Example 11

5-{2-[4-(2-Methoxy-phenyl)-piperazin-1-yl]-ethyl}-4-naphthalen-2-yl-2,4-dihydro-[1,2,4]triazol-3-one (E11)

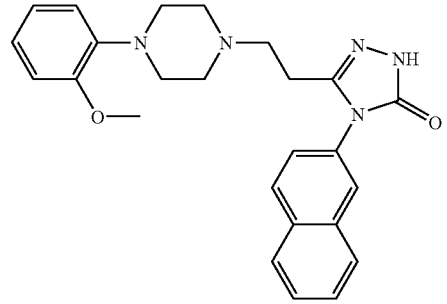

$^1$H NMR (400 MHz, DMSO-d6): $\delta_H$ 11.71 (1H, br., NH), 8.10-7.98 (4H, m, aryl), 6.68-6.50 (3H, m, aryl), 6.95-6.75 (4H, m, aryl), 3.72 (3H, s, OCH$_3$), 2.85-2.75 (4H, br., NCH$_2$), 2.70-2.65 (2H, m, CH$_2$), 2.55-2.45 (obscured by DMSO), 2.40-2.30 (4H, br., NCH$_2$).

LC-MS: Retention time 3.88 min, 94%, ES$^+$: 430 [MH]$^+$

Example 12

5-{2-[4-(2-Methoxy-phenyl)-piperazin-1-yl]-ethyl}-4-p-tolyl-2,4-dihydro-[1,2,4]triazol-3-one (E12)

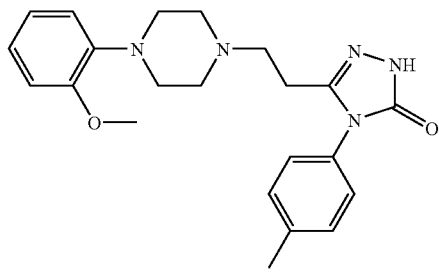

$^1$H NMR (400 MHz, DMSO-d6): $\delta_H$ 11.60 (1H, br., NH), 7.40-7.25 (4H, m, tolyl), 6.95-6.80 (4H, m, aryl), 3.75 (3H, s, OCH$_3$), 2.92-2.80 (4H, br., NCH$_2$), 2.70-2.65 (2H, m, CH$_2$), 2.55-2.45 (obscured by DMSO), 2.38 (6H, br.).

LC-MS: Retention time 3.63 min, 100%, ES$^+$: 394 [MH]$^+$

Example 13

4-Benzyl-5-{2-[4-(2-methoxy-phenyl)-piperazin-1-yl]-ethyl}-2,4-dihydro-[1,2,4]triazol-3-one (E13)

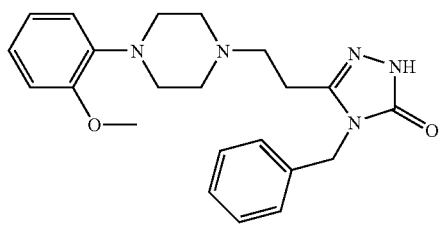

$^1$H NMR (400 MHz, DMSO-d6): 11.58 (1H, br. s, NH), 7.42-7.20 (5H, m, aryl), 6.98-6.80 (4H, m, aryl), 4.82 (2H, s, CH$_{2,benzyl}$), 3.78 (3H, s, OCH$_3$), 3.00-2.80 (4H, br., CH$_2$), 2.70-2.65 (4H, br., CH$_2$), 2.50-2.30 (4H, br., CH$_2$).

LC-MS: Retention time 3.54 min, 100%, ES$^+$: 394 [MH]$^+$

Example 14

4-(4-Isopropyl-phenyl)-5-{2-[4-(2-methoxy-phenyl)-piperazin-1-yl]-ethyl}-2,4-dihydro-[1,2,4]triazol-3-one (E14)

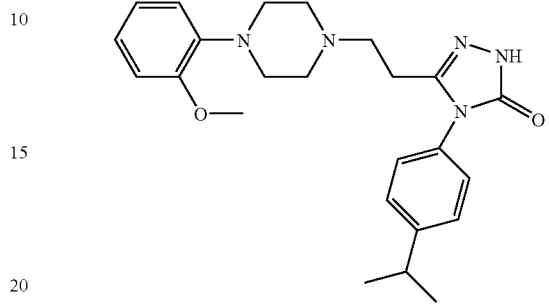

$^1$H NMR (400 MHz, DMSO-d6): $\delta_H$ 11.65 (1H, br. s, NH), 7.45-7.30 (4H, m, aryl), 7.00-6.75 (4H, m, aryl), 3.75 (3H, s, OCH$_3$), 3.00-2.75 (5H, m), 2.65-2.55 (2H, m), 2.52-2.45 (obscured by DMSO), 2.40-2.30 (4H, m), 1.25 (6H, d, J 7 Hz, iPr).

LC-MS: Retention time 4.138 min, 100%, ES$^+$: 422 [MH]$^+$

Example 15

4-(4-tert-Butyl-phenyl)-5-{2-[4-(2-methoxy-phenyl)-piperazin-1-yl]-ethyl}-2,4-dihydro-[1,2,4]triazol-3-one (E15)

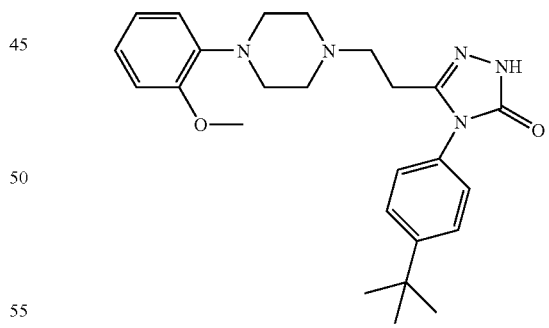

$^1$H NMR (400 MHz, DMSO-d6): $\delta_H$ 7.54 (2H, d, J 8.7 Hz, aryl), 7.32 (2H, d, J 8.5 Hz, aryl), 6.95-6.80 (4H, m, aryl), 3.74 (3H, s, OCH$_3$), 2.90-2.80 (4H, br., NCH$_2$), 2.62-2.58 (2H, m, CH$_3$), 2.55-2.45 (obscured by DMSO), 2.32 (9H, s, tBu).

LC-MS: Retention time 4.32 min, 100%, ES$^+$: 436 [MH]$^+$

Example 16

4-Indan-5-yl-5-{2-[4-(2-methoxy-phenyl)-piperazin-1-yl]-ethyl}-2,4-dihydro-[1,2,4]triazol-3-one (E16)

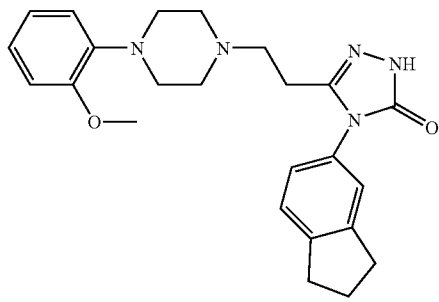

¹H NMR (400 MHz, DMSO-d6): δ_H 11.56 (1H, br., NH), 7.36 (1H, d, J 7.7 Hz, aryl), 7.23 (1H, s, indanyl), 7.11 (1H, d, J 8 Hz, aryl), 6.97-6.80 (4H, m, aryl), 3.75 (3H, s, OCH₃), 3.00-2.80 (8H, m), 2.58 (1H, m), 2.55-2.45 (obscured by DMSO), 2.11-2.02 (1H, m).

LC-MS: Retention time 3.93 min, 98%, ES⁺: 420 [MH]⁺

Example 17

4-(Cyclohexylmethyl)-5-{2-[4-(2-methoxyphenyl)piperazino]ethyl}-2,4-dihydro-3H-1,2,4-triazol-3-one (E17)

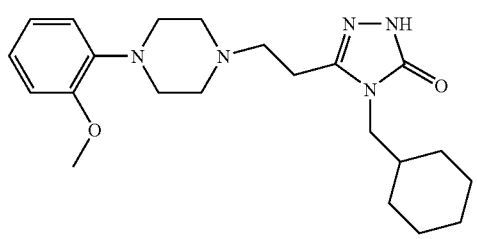

A suspension of N-(cyclohexylmethyl)-2-{3-[4-(2-methoxyphenyl)piperazino]propanoyl}-1-hydrazinecarboxamide D4 (0.40 g, 0.96 mmol) in 2M NaOH aqueous solution (10 mL) was heated at reflux for 7 hrs. The resulting precipitate was filtered, washed with water and diethyl ether to afford 0.22 g (57%) 4-(cyclohexylmethyl)-5-{2-[4-(2-methoxyphenyl)piperazino]ethyl}-2,4-dihydro-3H-1,2,4-triazol-3-one E17 as a white solid.

¹H NMR (400 MHz, DMSO-d6): δ_H 11.50-11.30 (1H, br. s, NH), 7.00-6.80 (4H, m, aryl), 3.75 (3H, s, OCH₃), 3.42 (2H, d, J 7.4 Hz, NCH₂CH-cyclohexyl), 3.05-2.85 (4H, br., NCH₂), 2.75-2.50 (8H, m), 1.75-1.50 (6H, m), 1.25-1.05 (3H, m), 1.04-0.85 (2H, m).

LC-MS: Retention time 3.92 min, 100%, ES⁺: 400 [MH]⁺

Examples 18-33

E18-E33 may be prepared in an analogous manner to E2, E10 and E17.

Example 18

5-{2-[4-(2-Methoxy-phenyl)-piperazin-1-yl]-ethyl}-4-(1-phenyl-ethyl)-2,4-dihydro-[1,2,4]triazol-3-one (E18)

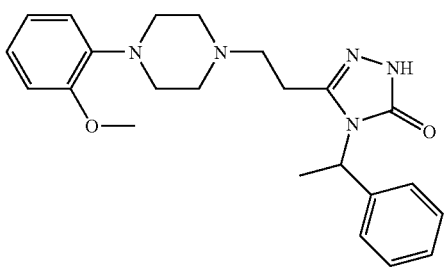

¹H NMR (400 MHz, CDCl₃): δ_H 9.79 (1H, br., NH), 7.40-7.28 (6H, m, aryl), 7.05-6.95 (1H, m, aryl), 6.95-6.83 (3H, m, aryl), 5.48 (1H, q, J 7 Hz, CH₃CH), 3.85 (3H, s, OCH₃), 3.25-3.00 (4H, br.), 2.95-2.40 (8H, br.), 1.90 (3H, d, J 7 Hz, CH₃CH).

LC-MS: Retention time 3.61 min, 100%, ES⁺: 408 [MH]⁺

Example 19

5-{2-[4-(2-Methoxy-phenyl)-piperazin-1-yl]-ethyl}-4-(1-phenyl-propyl)-2,4-dihydro-[1,2,4]triazol-3-one (E19)

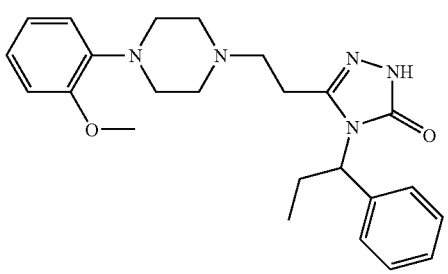

LC-MS: Retention time 3.86 min, 100%, ES⁺: 422 [MH]⁺

Example 20

4-(4-Chloro-benzyl)-5-{2-[4-(2-methoxy-phenyl)-piperazin-1-yl]-ethyl}-2,4-dihydro-[1,2,4]triazol-3-one (E20)

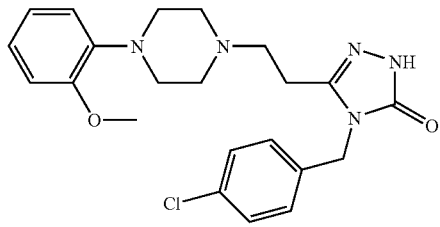

LC-MS: Retention time 3.75 min, 100%, ES$^+$: 428 [M($^{35}$Cl)H]$^+$, 430 [M($^{37}$Cl)H]$^+$

Example 21

4-(3,4-Dichloro-benzyl)-5-{2-[4-(2-methoxy-phenyl)-piperazin-1-yl]-ethyl}-2,4-dihydro-[1,2,4]triazol-3-one (E21)

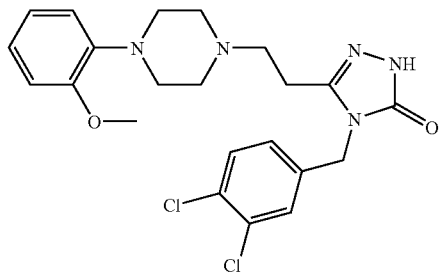

LC-MS: Retention time 3.97 min, 92.2%, ES$^+$: 462 [M($^{35}$Cl, $^{35}$Cl)H]$^+$, 464 [M($^{35}$Cl, $^{37}$Cl)H]$^+$

Example 22

4-(2-Ethoxy-benzyl)-5-{2-[4-(2-methoxy-phenyl)-piperazin-1-yl]-ethyl}-2,4-dihydro-[1,2,4]triazol-3-one (E22)

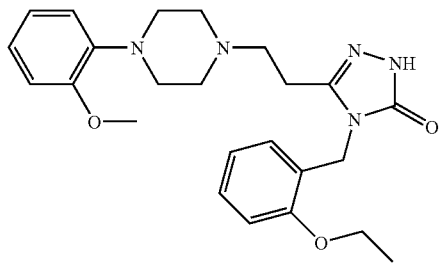

LC-MS: Retention time 3.78 min, 100%, ES$^+$: 438 [MH]$^+$

Example 23

5-{2-[4-(2-Methoxy-phenyl)-piperazin-1-yl]-ethyl}-4-(2-phenyl-cyclopropyl)-2,4-dihydro-[1,2,4]triazol-3-one (E23)

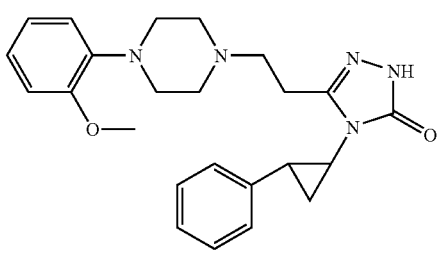

$^1$H NMR (400 MHz, CDCl$_3$): δ$_H$ 10.2 (1H, br., NH), 7.37-7.18 (5H, m, aryl), 7.05-6.98 (1H, m, aryl), 6.95-6.82 (3H, m, aryl), 3.88 (3H, s, OCH$_3$), 3.22-2.65 (13H, m and 3×br.), 2.55-2.45 (1H, m, CH$_{cyclopropyl}$), 1.78-1.70 (1H, m, CH$_{cyclopropyl}$), 1.62-1.55 (1H, m, CH$_{cyclopropyl}$).

LC-MS: Retention time 3.68 min, 100%, ES$^+$: 420 [MH]$^+$

Example 24

5-{2-[4-(2-Methoxy-phenyl)-piperazin-1-yl]-ethyl}-4-(2-methyl-benzyl)-2,4-dihydro-[1,2,4]triazol-3-one (E24)

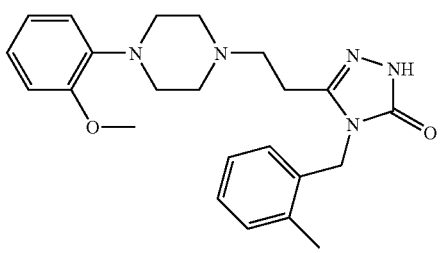

$^1$H NMR (400 MHz, CDCl$_3$): δ$_H$ 10.08 (1H, br., NH), 7.20-7.10 (3H, m, aryl), 7.05-6.95 (1H, m, aryl), 6.94-6.82 (4H, m, aryl), 4.88 (2H, s, CH$_{2, tolyl}$), 3.85 (3H, s, OCH$_3$), 3.20-3.00 (4H, br., CH$_2$), 2.80-2.55 (8H, br., CH$_2$), 2.33 (3H, s, CH$_{3, tolyl}$).

LC-MS: Retention time 3.62 min, 100%, ES$^+$: 408 [MH]$^+$

Example 25

4-(2,4-Dichloro-benzyl)-5-{2-[4-(2-methoxy-phenyl)-piperazin-1-yl]-ethyl}-2,4-dihydro-[1,2,4]triazol-3-one (E25)

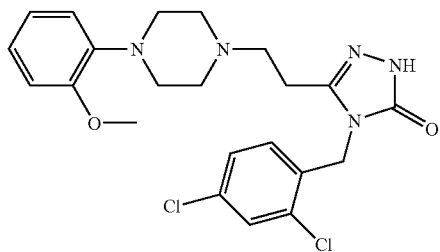

LC-MS: Retention time 4.06 min, 100%, ES$^+$: 462 [M($^{35}$Cl, $^{35}$Cl)H]$^+$, 464 [M($^{35}$Cl, $^{37}$Cl)H]$^+$

Example 26

4-(3-Fluoro-benzyl)-5-{2-[4-(2-methoxy-phenyl)-piperazin-1-yl]-ethyl}-2,4-dihydro-[1,2,4]triazol-3-one (E26)

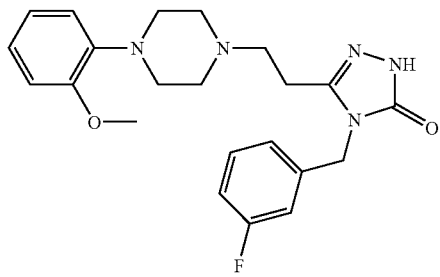

LC-MS: Retention time 3.51 min, 93.9%, ES$^+$: 412 [MH]$^+$

Example 27

5-{2-[4-(2-Methoxy-phenyl)-piperazin-1-yl]-ethyl}-4-(4-methyl-benzyl)-2,4-dihydro-[1,2,4]triazol-3-one (E27)

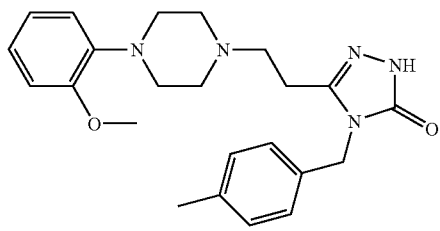

$^1$H NMR (400 MHz, CDCl$_3$): $\delta_H$ 10.10 (1H, br., NH), 7.25-7.11 (4H, m, aryl), 7.08-7.00 (1H, m, aryl), 6.95-6.82 (3H, m, aryl), 4.90 (2H, s, CH$_{2, tolyl}$) 3.85 (3H, s, OCH$_3$), 3.40-3.20 (4H, br., CH$_2$), 3.15-2.80 (8H, br., CH$_2$), 2.30 (3H, s, CH$_{3, tolyl}$).

LC-MS: Retention time 3.65 min, 100%, ES$^+$: 408 [MH]$^+$

Example 28

4-Benzhydryl-5-{2-[4-(2-methoxy-phenyl)-piperazin-1-yl]-ethyl}-2,4-dihydro-[1,2,4]triazol-3-one (E28)

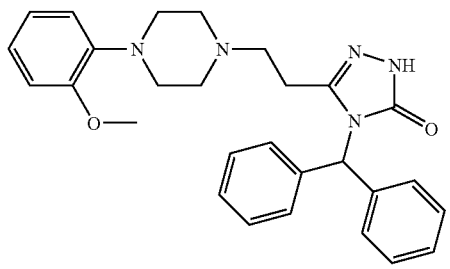

LC-MS: Retention time 4.22 min, 100%, ES$^+$: 470 [MH]$^+$

Example 29

4-Indan-1-yl-5-{2-[4-(2-methoxy-phenyl)-piperazin-1-yl]-ethyl}-2,4-dihydro-[1,2,4]triazol-3-one (E29)

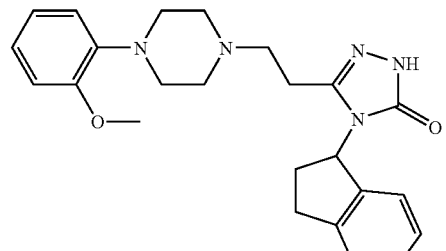

$^1$H NMR (400 MHz, CDCl$_3$): $\delta_H$ 9.95 (1H, br., NH), 7.35-7.20 (4H, m, aryl), 7.10-6.82 (4H, m, aryl), 5.82 (1H, m, J 8.2 Hz, indanyl), 3.87 (3H, s, OCH$_3$), 3.30-2.80 (10H, br.), 2.80-2.50 (4H, br.), 2.40-2.20 (2H, br.).

LC-MS: Retention time 3.68 min, 100%, ES$^+$: 420 [MH]$^+$

Example 30

4-(2-Fluoro-benzyl)-5-{2-[4-(2-methoxy-phenyl)-piperazin-1-yl]-ethyl}-2,4-dihydro-[1,2,4]triazol-3-one (E30)

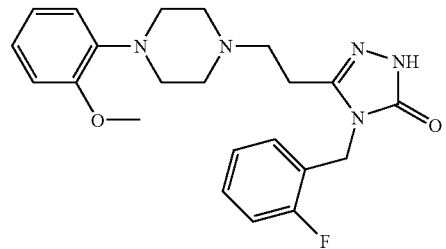

LC-MS: Retention time 3.51 min, 100%, ES$^+$: 412 [MH]$^+$

Example 31

4-(2-Methoxy-benzyl)-5-{2-[4-(2-methoxy-phenyl)-piperazin-1-yl]-ethyl}-2,4-dihydro-[1,2,4]triazol-3-one (E31)

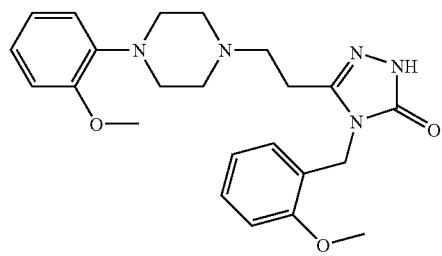

LC-MS: Retention time 3.48 min, 100%, ES$^+$: 424 [MH]$^+$

Example 32

4-(2-Chloro-benzyl)-5-{2-[4-(2-methoxy-phenyl)-piperazin-1-yl]-ethyl}-2,4-dihydro-[1,2,4]triazol-3-one (E32)

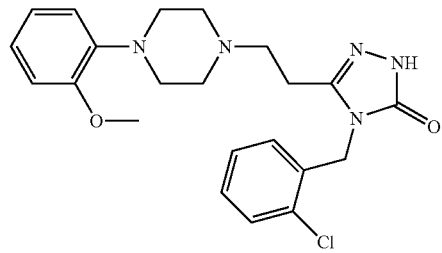

LC-MS: Retention time 3.73 min, 100%, ES$^+$: 428 [M($^{35}$Cl)H]$^+$, 430 [M($^{37}$Cl)H]$^+$

Example 33

4-(3,4-Dichloro-phenyl)-5-{2-[4-(2-methoxy-phenyl)-piperazin-1-yl]-ethyl}-2,4-dihydro-[1,2,4]triazol-3-one (E33)

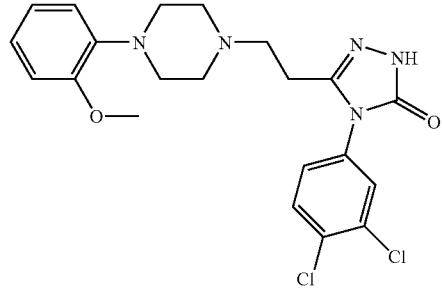

LC-MS: Retention time 3.98 min, 100%, ES$^+$: 448 [M($^{35}$Cl, $^{35}$Cl)H]$^+$, 450 [M($^{35}$Cl, $^{37}$Cl)H]$^+$

Examples 34-36

E34-E36 may be prepared in an analogous manner to E37.

Example 34

4-(4-Bromo-phenyl)-5-{2-[4-(2-methoxy-phenyl)-piperazin-1-yl]-propyl}-2,4-dihydro-[1,2,4]triazol-3-one (E34)

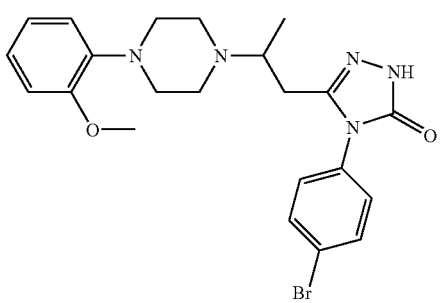

$^1$H NMR (400 MHz, CDCl$_3$): δ$_H$ 9.68 (1H, br., NH), 7.65 (2H, d, J 8.7 Hz, aryl), 7.22 (2H, d, J 8.8 Hz, aryl), 7.05-6.95 (1H, m, aryl), 6.92-6.80 (3H, m, aryl), 3.83 (3H, s, OCH$_3$), 3.10-2.70 (6H, 2×br., CH$_2$), 2.68-2.40 (5H, m and br., CH$\overline{CH_3}$ and $\overline{CH_2}$), 1.70-1.65 (2$\overline{H}$, br., CH$_2$), 1.10-1.00 (3H, br., $\overline{CH_3}$).

LC-MS: Retention time 4.02 min, 99%, ES$^+$: 436 (30), 421(20), 411(45), 395(86), 393(55) [(M-Br)+H]$^+$, 379(95), 364(50), 363 (100).

Example 35

4-(3-{2-[4-(2-Methoxy-phenyl)-piperazin-1-yl]-propyl}-5-oxo-1,5-dihydro-[1,2,4]triazol-4-yl)-benzoic acid (E35)

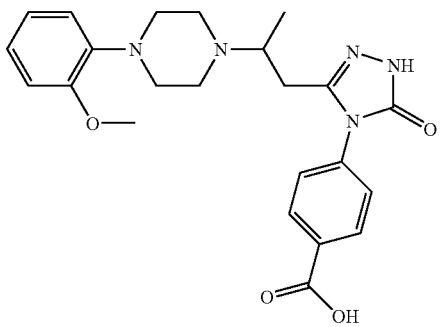

LC-MS: Retention time 2.08 min, 100%, ES$^+$: 438 [M+H]$^+$

Example 36

4-Cyclohexylmethyl-5-{2-[4-(2-methoxy-phenyl)-piperazin-1-yl]-propyl}-2,4-dihydro-[1,2,4]triazol-3-one (E36)

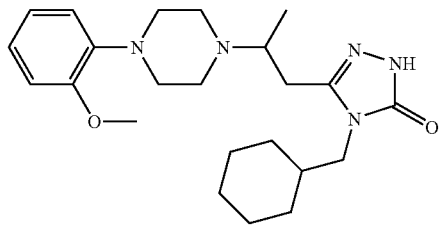

$^1$H NMR (400 MHz, CDCl$_3$): δ$_H$ 9.55 (1H, br. s, NH), 7.05-6.85 (4H, m, aryl), 3.85 (3H, s, OCH$_3$), 3.50-3.40 (2H, d, J 7.4 Hz, NCH$_{2, \, cyclohexyl}$), 3.15-3.05 (4H, br., NCH$_2$), 2.84-2.75 (4H, m), 2.50-2.40 (1H, m, CHCH$_3$), 1.80-1.60 (8H, m), 1.25-1.10 (6H, m), 1.05-0.90 (2H, m).

LC-MS: Retention time 3.98 min, 96%, ES$^+$: 414 [M+H]$^+$

Example 37

4-(Cyclohexylmethyl)-5-{2-[4-(2-methoxyphenyl)piperazin-1-yl]propyl}-2-methyl-2,4-dihydro-3H-1,2,4-triazol-3-one (E37)

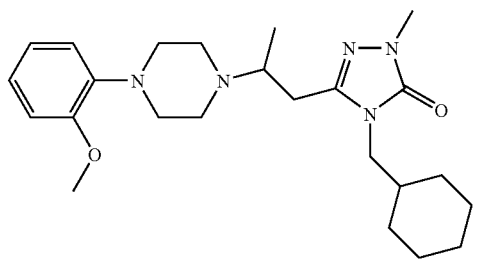

To a slurry of 4-(cyclohexylmethyl)-5-{2-[4-(2-methoxyphenyl)piperazin-1-yl]propyl}-2,4-dihydro-3H-1,2,4-triazol-3-one D14 (50 mg, 0.121 mmol) and PS-BEMP (83 mg, 0.1820 mmol, 2.2 mmol/g) in MeCN (2 mL), MeI (11.5 µL, 0.182 mmol) was added and the mixture was shaken at room temperature for 64 h. The resin was filtered and the filtrate was evaporated under reduced pressure. The resulting yellow oil was purified by flash chromatography (Biotage Isolute SI, 1 g column, gradient DCM to 1% MeOH in DCM) and afforded 25 mg (48%) 4-(cyclohexylmethyl)-5-{2-[4-(2-methoxyphenyl)piperazin-1-yl]propyl}-2-methyl-2,4-dihydro-3H-1,2,4-triazol-3-one E37 as a white solid.

LC-MS: Retention time 4.41 min, 100%, ES$^+$: 428 [MH]$^+$

Example 38

N-[3-(4-{2-[4-(Cyclohexylmethyl)-5-oxo-4,5-dihydro-1H-1,2,4-triazol-3-yl]ethyl}piperazin-1-yl)phenyl]acetamide (E38)

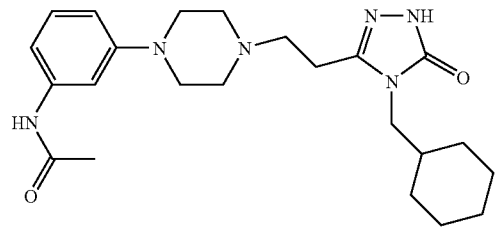

A solution of 5-{2-[4-(3-aminophenyl)piperazin-1-yl]ethyl}-4-(cyclohexylmethyl)-2,4-dihydro-3H-1,2,4-triazol-3-one D10 (0.13 g, 0.34 mmol) in pyridine (2 mL) was cooled to 0° C. and acetyl chloride (0.025 mL, 0.029 g, 0.36 mmol) was added. The reaction mixture was stirred at 0° C. for 18 hrs and then evaporated to dryness. The residue was purified by flash chromatography (Silica gel 60 Å, 45 µm, 10% methanol in dichloromethane) and afforded 0.015 g (10%) N-[3-(4-{2-[4-(cyclohexylmethyl)-5-oxo-4,5-dihydro-1H-1,2,4-triazol-3-yl]ethyl}piperazin-1-yl)phenyl]acetamide E38 as an orange oil.

$^1$H NMR (400 MHz, CDCl$_3$): δ$_H$ 10.03-9.98 (1H, br., NH), 7.40 (1H, s, CH$_3$CONH), 7.30 (1H, app. s, aryl), 7.19-7.13 (1H, m, aryl), 6.84 (1H, d, J 7.7 Hz, aryl), 6.62 (1H, d, J 7.8 Hz, aryl), 3.44 (2H, d, J 7.4 Hz, NCH$_2$CH-cyclohexyl), 3.23-3.17 (4H, m, NCH$_2$), 2.85-2.63 (8H, m), 2.15 (3H, s, CH$_3$), 1.82-1.60 (6H, m), 1.31-1.10 (3H, m), 1.05-0.90 (2H, m).

LC-MS: Retention time 3.14 min, 98%, ES$^+$: 427 [MH]$^+$

Examples 39-40

E39-E40 may be prepared in an analogous manner to E38.

Example 39

N-(3-{4-[3-(4-Cyclohexylmethyl-5-oxo-4,5-dihydro-1H-[1,2,4]triazol-3-yl)-propyl]-piperazin-1-yl}-phenyl)-acetamide (E39)

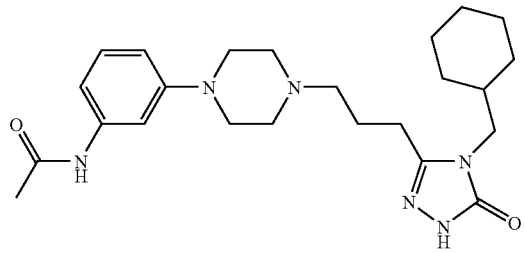

$^1$H NMR (400 MHz, DMSO-d6): δ$_H$ 11.32 (1H, br. s, NNH), 9.75 (1H, br. s, NHCOCH$_3$), 7.22 (1H, br. s, aryl), 7.10 (1H, app. t, aryl), 7.00 (1H, d, J 8 Hz, aryl), 7.62 (1H, d, J 8 Hz, aryl), 3.40 (2H, d, J 7.5 Hz, CH$_2$CH), 3.15-3.00 (4H, br., C H$_2$), 2.65-2.45 (obscured by DMSO), 2.40-2.30 (1H, t, J 6.7 Hz, CH$_2$CH), 2.02 (3H, s, CH$_3$), 1.75-1.50 (9H, m), 1.25-1.10 (5H, m), 1.10-0.90 (1H, m).

LC-MS: Retention time 3.19 min, 92%, ES$^+$: 441 [M+H]$^+$

Example 40

N-(3-{4-[4-(4-Cyclohexylmethyl-5-oxo-4,5-dihydro-1H-[1,2,4]triazol-3-yl)-butyl]-piperazin-1-yl}-phenyl)-acetamide (E40)

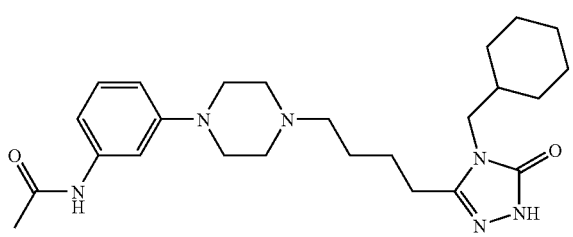

$^1$H NMR (400 MHz, DMSO-d6): δ$_H$ 11.30 (1H, br. s, NN H), 9.72 (1H, br. s, NHCOCH$_3$), 7.22 (1H, br. s, aryl), 7.12 (1H, app. t, aryl), 7.00 (1H, d, J 8 Hz, aryl), 7.60 (1H, d, J 8 Hz, aryl), 3.40 (2H, d, J 7.5 Hz, CH$_2$CH), 3.15-3.05 (4H, br., CH$_2$), 2.65-2.45 (obscured by DMSO), 2.40-2.30 (1H, br., CH$_2$CH), 2.02 (3H, s, CH$_3$), 1.75-1.50 (11H, m), 1.25-1.10 (5H, m), 1.10-0.90 (1H, m).

LC-MS: Retention time 3.21 min, 100%, ES$^+$: 455 [M+H]$^+$

Example 41

N-[3-(4-{2-[4-(Cyclohexylmethyl)-1-methyl-5-oxo-4,5-dihydro-1H-1,2,4-triazol-3-yl]ethyl}piperazino)phenyl]acetamide (E41)

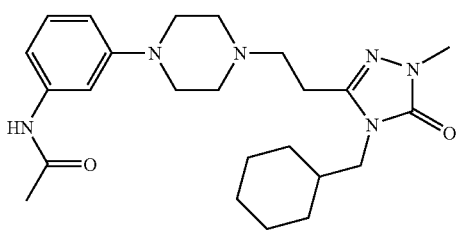

To a solution of 5-{2-[4-(3-aminophenyl)piperazino]ethyl}-4-(cyclohexylmethyl)-2-methyl-2,4-dihydro-3H-1,2,4-triazol-3-one (D16; 450 mg, 1.129 mmol) in dry pyridine (5 mL), acetic anhydride (0.112 mL, 1.185 mmol) was added at room temperature. The reaction mixture was stirred for 1 h, toluene (30 mL) was added and the solvents were removed in vacuo to afford a light-brown solid. Purification by preparative LC-MS afforded 133 mg (27%) of the title compound as a light brown powder.

$^1$H NMR (400 MHz, CD$_3$OD): δ$_H$ 7.40 (1H, app. s, CH$_3$CONH), 7.28 (1H, app. t, aryl), 7.10-7.06 (1H, d, J 6.9 Hz, aryl), 6.85-6.80 (1H, d, J 6.5 Hz, aryl), 3.62 (2H, d, J 7.4 Hz, NCH$_2$cyclohexyl), 3.50 (3H, s, NCH$_3$), 3.32-3.28 (4H, m, NCH$_2$), 3.00-2.80 (8H, m), 2.21 (3H, s, CH$_3$), 1.90-1.70 (6H, m), 1.40-1.30 (3H, m), 1.20-1.05 (2H, m).

LC-MS: Retention time 4.64 min, 100%, ES$^+$: 441 [MH]$^+$

Example 42

4-(Cyclohexylmethyl)-5-{2-[4-(2-methoxyphenyl)piperazino]ethyl}-2-methyl-2,4-dihydro-3H-1,2,4-triazol-3-one (E42)

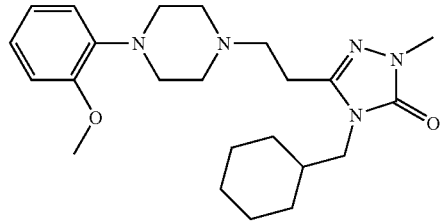

To a slurry of PS-BEMP (0.95 g, 2.08 mmol, 2.2 mmol/g) and 4-(cyclohexylmethyl)-5-{2-[4-(2-methoxyphenyl)piperazino]ethyl}-2,4-dihydro-3H-1,2,4-triazol-3-one (E17; 415 mg, 1.028 mmol) in MeCN (20 mL), methyl iodide (0.13 mL, 2.08 mmol) was added and the reaction mixture was stirred at room temperature for 2 days. The resin was filtered, washed with MeOH (25 mL) and the solvent was evaporated in vacuo to afford 560 mg crude yellow glassy solid. This was dissolved in DCM (3 mL) and purified by flash chromatography (Flash Master, Biotage Isolute SI, 20 g column, gradient 0-10% MeOH in DCM over 30 min) to afford 350 mg of a light yellow oil. Further purification by preparative LC-MS afforded 190 mg (44%) of the title compound as a glassy solid.

$^1$H NMR (400 MHz, DMSO-d6): δ$_H$ 7.00-6.85 (4H, m, aryl), 3.78 (3H, s, OCH$_3$), 3.4 (2H, d, J 7.4 Hz, NCH$_2$cyclohexyl), 3.28 (3H, s, NCH$_3$), 3.00-2.90 (4H, br., NCH$_2$), 2.68 (4H, s), 2.62-2.55 (4H, br., NCH$_2$), 1.72-1.50 (6H, m), 1.22-1.05 (3H, m), 1.00-0.85 (2H, m).

LC-MS: Retention time 5.80 min, 100%, ES$^+$: 414 [MH]$^+$

Example 43

4-(Cyclohexylmethyl)-2-ethyl-5-{2-[4-(2-methoxyphenyl)piperazino]ethyl}-2,4-dihydro-3H-1,2,4-triazol-3-one (E43)

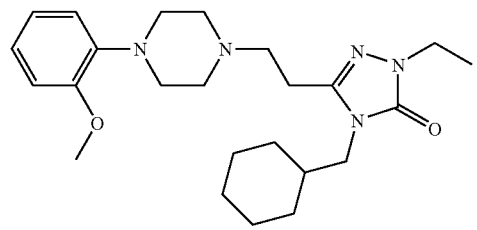

To a slurry of PS-BEMP (0.682 g, 1.50 mmol, 2.2 mmol/g) and 4-(cyclohexylmethyl)-5-{2-[4-(2-methoxyphenyl)piperazino]ethyl}-2,4-dihydro-3H-1,2,4-triazol-3-one (E17; 300 mg, 0.75 mmol) in MeCN (10 mL), ethyl iodide (0.12 mL, 1.50 mmol) was added and the reaction mixture was stirred at room temperature for 3 days. The resin was filtered, washed with MeOH (10 mL) and the solvent was evaporated in vacuo to afford 280 mg crude foamy solid. Purification by preparative LC-MS afforded 190 mg (59%) of the title compound as a glassy solid.

$^1$H NMR (400 MHz, DMSO-d6): $\delta_H$ 7.00-6.85 (4H, m, aryl), 3.78 (3H, s, OCH$_3$), 3.65 (2H, q, J 7.2 Hz, CH$_2$CH$_3$), 3.42 (2H, d, J 7.4 Hz, NCH$_2$cyclohexyl), 3.28 (3H, s, NCH$_3$), 3.00-2.90 (4H, br., NCH$_2$), 2.68 (4H, s), 2.62-2.55 (4H, br., NCH$_2$), 1.70-1.50 (6H, m), 1.22-1.10 (6H, m), 1.00-0.85 (2H, m).

LC-MS: Retention time 6.24 min, 96.24%, ES$^+$: 428 [MH]$^+$

Binding Assays:

5HT$_{1A}$ Receptor Assay:

The determination of binding of the ligand with 5HT$_{1A}$ receptor was carried out according to the procedures described in Martin GR and Humphrey PPA. Neuropharmacol. 33: 261-273.

For competition binding, radiolabelled 1.5 nM [3H]8-OH-DPAT was incubated for 60 minutes at 25° C. with 5HT$_{1A}$ transfected human recombinant CHO cell membranes in 50 mM Tris-HCl, pH7.4, 0.1% Ascorbic acid, 10 mM MgSO4.7H2O and 0.5 mM EDTA and increasing concentrations of test compound. The non-specific ligand used was 10 mM Metergoline. Significance criteria were 50% of max stimulation or inhibition.

α1-Adrenergic Receptor Assay

The determination of binding of the ligand with α1-adrenergic receptor was carried out according to the procedures described in Greengrass P and Bremner R. Eur. J. Pharmacol. 1979, 55: 323-326.

For competition binding, radiolabelled 0.25 nM [3H]Prazosin was incubated for 30 minutes at 25° C. with al transfected wisatar rat cerebral cortex cell membranes in 50 mM Tris-HCl, pH7.4, 0.1% Ascorbic acid, 10 mM Pargyline and increasing concentrations of test compound. The non specific ligand used was 0.1 uM Prazosin. Significance criteria was 50% of max stimulation or inhibition.

Dopamine D2 Receptor Assay:

The determination of binding of the ligand with dopamine D2L receptor was carried out according to the procedures described in Grandy et al. Proc. Natl. Acad. Sci. 1989, 86: 9762-9766.

For competition binding, radiolabelled 0.16 nM [3H]Spiperone was incubated for 120 minutes at 25° C. with D2L transfected human recombinant CHO cells in 50 mM Tris-HCl, pH7.4, 150 mM NaCl, 1.4 mM Ascorbic acid, 0.001% BSA and increasing concentrations of test compound. The non-specific ligand used was 10 mM haloperidol. Significance criteria was 50% of max stimulation or inhibition.

Results:

Affinity Analysis

The compounds of Examples 1-43 were tested in the 5HT$_{1A}$ Receptor Assay and demonstrated the following levels of potency:

| Affinity for human 5HT1A (nM) | Example Numbers |
|---|---|
| <10 | 8, 9, 10, 13, 17, 19, 20, 21, 23, 25, 27, 28, 29, 31, 33, 36, 37, 41-43 |
| >10 | 1-7, 11, 12, 14-16, 18, 22, 24, 26, 30, 32, 34, 35, 38, 39, 40 |
| >300 | 1, 5, 34, 35 |

Selectivity Analysis

The compounds of Examples 37, 38 and 39 were additionally tested in the α1-adrenergic receptor assay and demonstrated an affinity for 5HT$_{1A}$ that is more than fifty times greater than their affinity for α1-adrenergic receptors. The compounds of Examples 37 and 38 were also tested in the Dopamine D2 receptor assay and demonstrated an affinity for 5HT$_{1A}$ that is more than fifty times greater than their affinity for dopamine D2 receptors. Furthermore, Example 41 was also tested in the Dopamine D2 receptor assay and demonstrated an affinity for 5HT$_{1A}$ that is more than a thousand times greater than its affinity for dopamine D2 receptors.

Efficacy Analysis

Selected compounds were tested for 5HT$_{1A}$ agonist activity using a GTPγS assay.

GTPγS binding for 5HT1A was determined according to the procedures of Adlersberg et al. J Neurosci. Res. 2000, 61(6): 674-685. Compounds were incubated for 30 minutes at 30° C. in 20 mM HEPES, pH7.4, 100 mM NaCl, 10 mM MgCl2, 1 mM DTT, 1 mM EDTA with human CHO cells Chinese hamster. Quantitation of bound [$^{35}$S] GTPγS was determined with agonist significance criteria of >50% increase in bound [$^{35}$S] GTPγS relative to serotonin response.

The compounds of Examples 10, 21, 28, 33, 41 and 42 were shown to exhibit EC50s with potency greater than 200 nM.

Stability Analysis

Metabolic stability of selected compounds in human liver microsomes was assessed using the procedure described by Kuhnz and Gieschen, Drug Metab. Dispos. 1998, 26: 1120-1127. Compounds (1 μM) were measured by LC/MS following 0 and 60 minute incubations with human liver microsomes (0.3 mg/mL) at pH7.4 and 37° C.

The compounds of Examples 13, 17 and 26 demonstrated half lives of at least 1 hour in both rat and human liver microsomes.

The invention claimed is:

1. A compound of formula (I) or a pharmaceutically acceptable salt thereof:

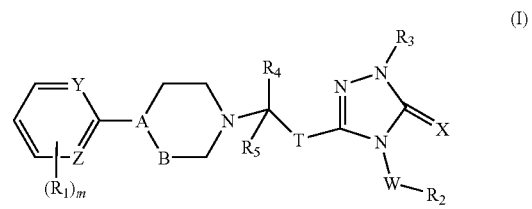

wherein
each R$^1$ independently represents halogen, —CF$_3$, —NO$_2$, C$_{1-6}$ alkoxy, —NR$^6$COR$^7$ or —NR$^6$SO$_2$R$^7$;
m represents an integer from 1 to 2, such that when m represents 2, said R$^1$ groups are not both -NR$^6$COR$^7$ or both —NR$^6$SO$_2$R$^7$ or both —NO$_2$;
R$^2$ represents C$_{3-8}$ cycloalkyl;
R$^3$ represents C$_{1-6}$ alkyl;
R$^4$, R$^5$, R$^6$ and R$^7$ independently represent hydrogen or C$_{1-6}$ alkyl;
-A-B— represents —C=CH— or —N—CH$_2$—;
T represents —CH$_2$—;
X represents an O or S atom;
Y and Z independently represent a CH or N atom; and
W represents —CH$_2$—.

2. The compound as defined in claim 1, wherein R$^1$ is present at the ortho and/or meta position.

3. The compound as defined in claim 2, wherein $R^1$ represents $C_{1-6}$ alkoxy, —$NR^6COR^7$, or —$NR^6SO_2R^7$.

4. The compound as defined in claim 3, wherein $R^1$ represents methoxy or ethanamide.

5. The compound as defined in claim 4, wherein $R^1$ represents ethanamide.

6. The compound as defined in claim 1, wherein $R^2$ represents cyclopentyl, cyclohexyl, cycloheptyl or cyclooctyl.

7. The compound as defined in claim 6, wherein $R^2$ represents cyclohexyl.

8. The compound as defined in claim 1, wherein $R^3$ represents methyl, ethyl, or isopropyl.

9. The compound as defined in claim 8, wherein $R^3$ represents methyl.

10. The compound as defined in claim 1, wherein $R^4$ represents hydrogen or methyl.

11. The compound as defined in claim 10, wherein $R^4$ represents hydrogen.

12. The compound as defined in claim 1, wherein $R^5$ represents hydrogen.

13. The compound as defined in claim 1, wherein -A-B- represents —N—$CH_2$—.

14. The compound as defined in claim 1, wherein X represents an O atom.

15. The compound as defined in claim 1, wherein Y and Z both represent —CH—.

16. The compound as defined in claim 1, wherein m represents 1.

17. The compound as defined in claim 1, which is a compound selected from:
   4-(Cyclohexylmethyl)-5-{2-[4-(2-methoxyphenyl)piperazin-1-yl]propyl}-2-methyl-2,4-dihydro-3H-1,2,4-triazol-3-one (E37);
   N-[3-(4-{2-[4-(Cyclohexylmethyl)-1-methyl-5-oxo-4,5-dihydro-1H-1,2,4-triazol-3-yl]ethyl }piperazino)phenyl]acetamide (E41);
   4-(Cyclohexylmethyl)-5-{2-[4-(2-methoxyphenyl)piperazino]ethyl}-2-methyl-2,4-dihydro-3H-1,2,4-triazol-3-one (E42); and
   4-(Cyclohexylmethyl)-2-ethyl-5-{2-[4-(2-methoxyphenyl)piperazino]ethyl}-2,4-dihydro-3H-1,2,4-triazol-3-one (E43); and
   or a pharmaceutically acceptable salt thereof.

18. The compound as defined in claim 17, which is N-[3-(4-{2-[4-(Cyclohexylmethyl)-1-methyl-5-oxo-4,5-dihydro-1H-1,2,4-triazol-3-yl]ethyl}piperazino)phenyl]acetamide (E41) or a pharmaceutically acceptable salt, thereof.

19. A method of treating a pain disorder, anxiety or depression which comprises administering to a patient in need thereof an effective amount of a compound of formula (I) as defined in claim 1 or a pharmaceutically acceptable salt thereof 20. A process for preparing a compound of formula (I) as defined in claim 1, which comprises:
   (a) preparing a compound of formula (I) wherein $R^1$ represents $C_{1-6}$ alkoxy and $R^3$ represents hydrogen which comprises ring closure of a compound of formula (II):

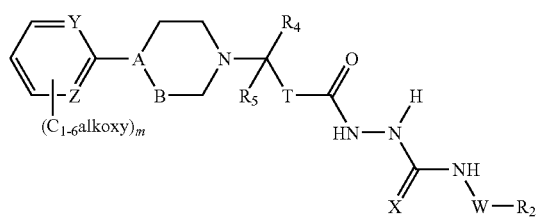

wherein $R^2$, $R^4$, $R^5$, -A-B-, T, X, Y, Z, W and m are as defined in claim 1 or:
   (b) preparing a compound of formula (I) wherein m represents 1, $R^1$ represents —$NR^6COR^7$ and $R^3$ represents hydrogen which comprises reacting a compound of formula (III),:

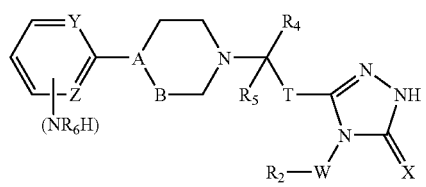

with a compound of formula $L^1COR^7$,
   wherein $L^1$ represents a suitable leaving group such as chlorine, and $R^2$, $R^4$, $R^5$, $R^6$, $R^7$, -A-B—, T, X, Y, Z and W are as defined in claim 1.

* * * * *